(12) United States Patent
Adesokan

(10) Patent No.: US 12,037,651 B2
(45) Date of Patent: *Jul. 16, 2024

(54) MICROBIOME MARKERS AND USES THEREOF

(71) Applicant: Gnubiotics Sciences SA, Epalinges (CH)

(72) Inventor: Adeyemi Adesokan, Lausanne (CH)

(73) Assignee: Gnubiotics Sciences SA, Epalinges (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/727,465

(22) Filed: Apr. 22, 2022

(65) Prior Publication Data

US 2022/0240543 A1    Aug. 4, 2022

Related U.S. Application Data

(63) Continuation of application No. 17/276,473, filed as application No. PCT/IB2019/001013 on Sep. 13, 2019.

(60) Provisional application No. 62/751,416, filed on Oct. 26, 2018, provisional application No. 62/731,051, filed on Sep. 13, 2018.

(51) Int. Cl.
| | | |
|---|---|---|
| *C12Q 1/689* | (2018.01) | |
| *A23K 10/18* | (2016.01) | |
| *A23K 50/40* | (2016.01) | |
| *A61K 9/00* | (2006.01) | |
| *A61K 35/741* | (2015.01) | |
| *A61K 35/742* | (2015.01) | |
| *A61K 38/17* | (2006.01) | |
| *A61P 3/04* | (2006.01) | |
| *C12Q 1/02* | (2006.01) | |
| *A61K 35/00* | (2006.01) | |

(52) U.S. Cl.
CPC .............. *C12Q 1/689* (2013.01); *A23K 10/18* (2016.05); *A23K 50/40* (2016.05); *A61K 9/0053* (2013.01); *A61K 35/741* (2013.01); *A61K 35/742* (2013.01); *A61K 38/1735* (2013.01); *A61P 3/04* (2018.01); *C12Q 1/025* (2013.01); *A61K 2035/115* (2013.01); *C12Q 2600/106* (2013.01)

(58) Field of Classification Search
None
See application file for complete search history.

(56) References Cited

U.S. PATENT DOCUMENTS

| | | |
|---|---|---|
| 11,229,671 B2 | 1/2022 | Adesokan et al. |
| 2016/0281142 A1 | 9/2016 | Czarnecki-Maulden |
| 2018/0064140 A1* | 3/2018 | Li ........................ A23K 10/16 |

FOREIGN PATENT DOCUMENTS

| | | | |
|---|---|---|---|
| JP | 2008125500 A | * | 6/2008 |
| KR | 10-2015-0024116 A | | 3/2015 |
| WO | WO 2014/145958 A2 | | 9/2014 |

OTHER PUBLICATIONS

Schomig et al., "An optimized purification process for porcine gastric mucin with preservation of its native functional properties", RSC Advances, vol. 6, pp. 44932-44943 (Year: 2016).*
Fischer, Manuela M., et al. "Effects of obesity, energy restriction and neutering on the faecal microbiota of cats." *British Journal of Nutrition* 118.7 (2017): 513-524.
Forster, Genevieve M., et al. "A comparative study of serum biochemistry, metabolome and microbiome parameters of clinically healthy, normal weight, overweight, and obese companion dogs." *Topics in companion animal medicine* 33.4 (2018): 126-135.
Li, Qinghong, et al. "Effects of the dietary protein and carbohydrate ratio on gut microbiomes in dogs of different body conditions." MBio 8.1 (2017): e01703-16.
Park, H.-J., et al. "Association of obesity with serum leptin, adiponectin, and serotonin and gut microflora in beagle dogs." *Journal of Veterinary Internal Medicine* 29.1 (2015): 43-50.
Salas-Mani, Anna, et al. "Fecal microbiota composition changes after a BW loss diet in Beagle dogs." *Journal of animal science* 96.8 (2018): 3102-3111.
Handl, Stefanie, et al. "Faecal microbiota in lean and obese dogs." *FEMS microbiology ecology* 84.2 (2013): 332-343.
International Preliminary Report on Patentability issued in International Application No. PCT/IB2019/001013, dated Mar. 9, 2021.
Extended European Search Report issued in Application No. 211755160.0-1118, dated Jul. 20, 2021.
Examination Report issued in EP Application No. 19 812 838.1-1118, dated Feb. 12, 2021.
Corrected Notice of Allowability Issued in U.S. Appl. No. 17/328,849, dated Nov. 4, 2021.
Notice of Allowance Issued in U.S. Appl. No. 17/328,849, dated Oct. 20, 2021.
Examination Report from EP Patent Application No. 21175516.0 dated Mar. 9, 2023, 7 pages.
Qinghong Li et al: "Effects of the Dietary Protein and Carbohydrate Ratio on Gut Microbiomes in Dogs of Different Body Conditions", MBIO, vol. 8, No. 1, Jan. 24, 2017 (Jan. 24, 2017).
Garcia-Mazcorro, Jose et al., Effect of a multi-species synbiotic formulation on fecal bacterial microbiota of healthy cats and dogs as evaluated by pyrosequencing, FEMS Microbiol. Ecol., pp. 542-554, 78, 2011.
Hooda, Seema et al., The gut microbiome of kittens is affected by dietary protein:carbohydrate ratio and associated with blood metabolite and hormone concentrations, British Journal of Nutrition, pp. 1637-1646, 109, 2013.

(Continued)

Primary Examiner — Michelle F. Paguio Frising
(74) Attorney, Agent, or Firm — Foley & Lardner LLP

(57) ABSTRACT

Bacterial species acting as biomarkers for obesity in domesticated cats and/or dogs are disclosed herein. Also disclosed are methods for diagnosing and/or treating cats and/or dogs having obesity or a predisposition to obesity as well as methods of screening for agents to treat or prevent obesity.

18 Claims, 33 Drawing Sheets

(56) References Cited

OTHER PUBLICATIONS

Masuoka, Hiroaki et al., Transition of the intestinal microbiota of cats with age, PLOS One, 12(8), Aug. 2017.
Non-Final Office Action on U.S. Appl. No. 17/276,473 DTD Mar. 22, 2024.

* cited by examiner

| Name | Status | BW | BCS |
|---|---|---|---|
| ASH – LC8 | Lean | 4,24 | 5 |
| JULIO – LC7 | Lean | 4,35 | 5 |
| MICHAEL – LC5 | Lean | 4,87 | 5 |
| MAMASBOY – LC6 | Lean | 4,07 | 5 |
| MONSTER – LC3 | Lean | 5,53 | 5 |
| NICKEL- LC4 | Lean | 4,7 | 5 |
| SLIM – LC2 | Lean | 4,35 | 5 |
| TIGER – LC1 | Lean | 4,42 | 5 |
| ASH – OC8 | Overweight | 9,10 | 9 |
| JULIO – OC7 | Overweight | 7,41 | 7 |
| MICHAEL – OC5 | Overweight | 6,80 | 7 |
| MAMASBOY – OC6 | Overweight | 8,10 | 8,5 |
| MONSTER – OC3 | Overweight | 7,10 | 7 |
| NICKEL – OC4 | Overweight | 7,15 | 7,5 |
| SLIM – OC2 | Overweight | 6,25 | 6,5 |
| TIGER – OC1 | Overweight | 6,72 | 7 |

| Name | Animal | Group | Sample ID | BW (kg) | BSC |
|---|---|---|---|---|---|
| Arya | Dog | Lean | LD1 | 10.72 | 6 |
| Cersei | Dog | Lean | LD2 | 10.65 | 5 |
| Dany | Dog | Lean | LD3 | 10.68 | 6.5 |
| Gilly | Dog | Lean | LD4 | 10.42 | 6 |
| Karsi | Dog | Lean | LD5 | 11.3 | 6.5 |
| Lysa | Dog | Lean | LD6 | 11.27 | 5.5 |
| Meera | Dog | Lean | LD7 | 10.5 | 5 |
| Osha | Dog | Lean | LD8 | 10.68 | 5.5 |
| Sansa | Dog | Lean | LD9 | 8.72 | 4 |
| Yara | Dog | Lean | LD10 | 8.62 | 4 |
| Arya | Dog | Obese | OD1 | 12.85 | 7.5 |
| Cersei | Dog | Obese | OD2 | 13.8 | 7 |
| Dany | Dog | Obese | OD3 | 13.4 | 8.5 |
| Gilly | Dog | Obese | OD4 | 13.6 | 8 |
| Karsi | Dog | Obese | OD5 | 14.5 | 8.5 |
| Lysa | Dog | Obese | OD6 | 14.3 | 8.5 |
| Meera | Dog | Obese | OD7 | 12.7 | 5.5 |
| Osha | Dog | Obese | OD8 | 13.35 | 7 |
| Sansa | Dog | Obese | OD9 | 12.15 | 6.5 |
| Yara | Dog | Obese | OD10 | 12.45 | 7.5 |

FIG. 1

| | SampleName | LibraryCount | GFPcount | ConditionsSummary | Weight |
|---|---|---|---|---|---|
| 1 | NoProbeNegativeControl1 | 4 | 0 | only water and buffer | noprobenegativecontrol |
| 2 | NoProbeNegativeControl2 | 28 | 0 | only water and buffer | noprobenegativecontrol |
| 3 | NoProbeNegativeControl3 | 492 | 0 | only water and buffer | noprobenegativecontrol |
| 4 | NotargetControl4 | 477468 | 24 | no sample, only calib. St and probes | notargetcontrol |
| 5 | NotargetControl5 | 289640 | 9 | no sample, only calib. St and probes | notargetcontrol |
| 6 | Notemplatecontrol6 | 440258 | 22 | no sample, only calib. St and probes | notemplatecontrol |
| 7 | Sample-LC1 | 1950872 | 24 | Tiger | Lean |
| 8 | Sample-LC2 | 1523246 | 11 | Slim | Lean |
| 9 | Sample-LC3 | 2411406 | 17 | Monster | Lean |
| 10 | Sample-LC4 | 1842124 | 14 | Nickie | Lean |
| 11 | Sample-LC5 | 1649230 | 19 | Michael | Lean |
| 12 | Sample-LC6 | 1678308 | 18 | MamasBoy | Lean |
| 13 | Sample-LC7 | 2016058 | 14 | Julio | Lean |
| 14 | Sample-LC8 | 1724618 | 14 | Ash | Lean |
| 15 | Sample-OC1 | 2296770 | 17 | Tiger | Obese |
| 16 | Sample-OC2 | 1925266 | 13 | Slim | Obese |
| 17 | Sample-OC3 | 2462088 | 17 | Monster | Obese |
| 18 | Sample-OC4 | 2291274 | 12 | Nickie | Obese |
| 19 | Sample-OC5 | 2130864 | 15 | Michael | Obese |
| 20 | Sample-OC6 | 2521962 | 13 | MamasBoy | Obese |
| 21 | Sample-OC7 | 2167476 | 20 | Julio | Obese |
| 22 | Sample-OC8 | 2169488 | 21 | Ash | Obese |

FIG. 10A

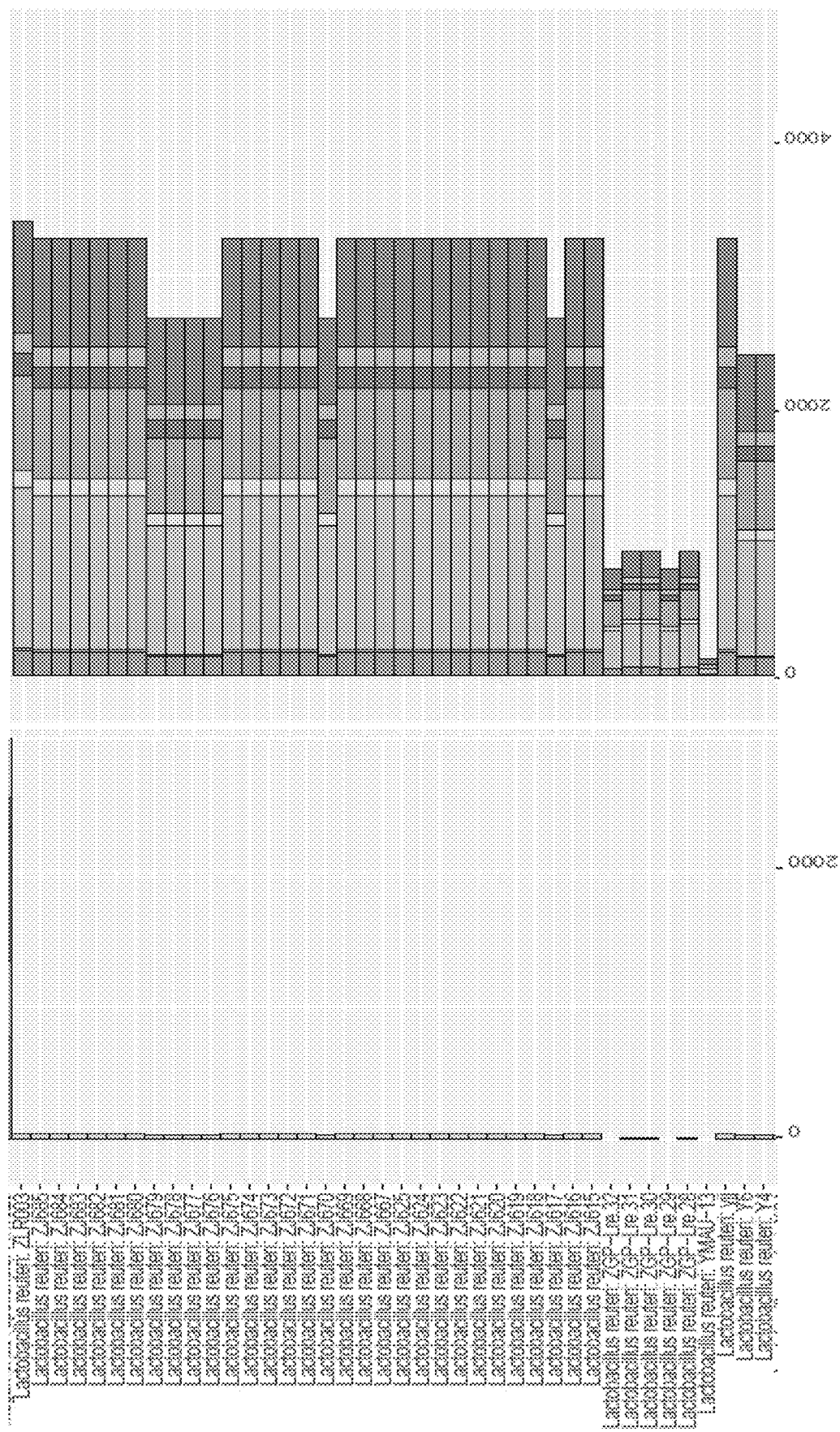

MICROBIOME MARKERS AND USES THEREOF

CROSS-REFERENCE TO RELATED APPLICATIONS

This application is a continuation application of co-pending U.S. application Ser. No. 17/276,473, filed Mar. 15, 2021, which is a national stage filing under 35 U.S.C. 371 of International Application No.: PCT/IB2019/001013, filed Sep. 13, 2019, which claims the benefit of U.S. Provisional Application No. 62/731,051, filed on Sep. 13, 2018, and U.S. Provisional Application No. 62/751,416, filed on Oct. 26, 2018. The entire teachings of the above applications are incorporated herein by reference.

BACKGROUND OF THE INVENTION

Obesity in domesticated animals is a growing problem. According to recent findings, more than 45% of dogs and 58% of cats can be classified as overweight or obese. As in humans, it is known that the gut microbiome is altered in obese animals compared to lean animals, and that modulation of the gut microbiome may be an effective method for treating and preventing obesity. However, little research has been done to understand the microbiome composition of obese versus lean domesticated animals.

SUMMARY OF THE INVENTION

It the work described herein, key microbiome species and strains that are differentially expressed in lean versus obese domesticated animals are identified. These key microbiome species and strains may be considered markers of leanness or obesity.

Disclosed herein are methods of treating obesity in a domesticated cat comprising one or more of the following: increasing the population of one or more bacterial species selected from *Megasphaera elsdenii, Megamonas rupellensis, Megamonas funiformis, Megamonas hypermegale*, and *Bacteroides coprophilus* in the gut of the cat to a level over a pre-determined threshold for the selected bacterial species; or decreasing the population of one or more bacterial species selected from *Lactobacillus reuteri* and *Blautia schinkii* in the gut of the cat to a level below a pre-determined threshold for the selected bacterial species.

Also disclosed herein are methods of selecting and treating a domesticated cat for obesity or a predisposition to obesity comprising the steps of: (a) selecting a domesticated cat on the basis of it having one or more of: (i) a gut population of one or more bacterial species selected from *Megasphaera elsdenii, Megamonas rupellensis, Megamonas funiformis, Megamonas hypermegale*, and *Bacteroides coprophilus* at a level below a pre-determined threshold for the selected bacterial species; and/or (ii) a gut population of one or more bacterial species selected from *Lactobacillus reuteri* and *Blautia schinkii* at a level above a pre-determined threshold for the selected bacterial species; and (b) treating the selected cat for obesity.

Disclosed herein are methods of identifying a domesticated cat for treatment with an anti-obesity agent comprising the step of determining if the cat has one or more of: a gut population of one or more bacterial species selected from *Megasphaera elsdenii, Megamonas rupellensis, Megamonas funiformis, Megamonas hypermegale*, and *Bacteroides coprophilus* at a level below a pre-determined threshold for the selected bacterial species; and/or a gut population of one or more bacterial species selected from *Lactobacillus reuteri* and *Blautia schinkii* at a level above a pre-determined threshold for the selected bacterial species, thereby identifying the cat for treatment with the anti-obesity agent.

Also disclosed herein are methods of diagnosing a domesticated cat for obesity or a predisposition to obesity comprising the steps of: (a) determining if the cat has one or more of: (i) a gut population of one or more bacterial species selected from *Megasphaera elsdenii, Megamonas rupellensis, Megamonas funiformis, Megamonas hypermegale*, and *Bacteroides coprophilus* at a level below a pre-determined threshold for the selected bacterial species; and/or (ii) a gut population of one or more bacterial species selected from *Lactobacillus reuteri* and *Blautia schinkii* at a level above a pre-determined threshold for the selected bacterial species; and thereby diagnosing the domesticated cat for obesity or a predisposition to obesity.

In some embodiments, the method of diagnosing a domesticated cat for obesity or a predisposition to obesity comprising further comprises the step of treating the cat for obesity if one or more of: (a) the gut population of one or more bacterial species selected from *Megasphaera elsdenii, Megamonas rupellensis, Megamonas funiformis, Megamonas hypermegale*, and *Bacteroides coprophilus* is at a level below a pre-determined threshold for the selected bacterial species; and/or (b) the gut population of one or more bacterial species selected from *Lactobacillus reuteri* and *Blautia schinkii* is at a level above a pre-determined threshold for the selected bacterial species.

Also disclosed herein are methods of determining the efficacy of an obesity treatment in a domesticated cat comprising the steps of: (a) determining at a time during treatment one or more of: (i) the gut population level of one or more bacterial species selected from *Megasphaera elsdenii, Megamonas rupellensis, Megamonas funiformis, Megamonas hypermegale*, and *Bacteroides coprophilus* in the cat; and/or (ii) the gut population level of one or more bacterial species selected from *Lactobacillus reuteri* and *Blautia schinkii* in the cat; and (b) comparing the determined gut population of the selected bacterial species to a gut population level of the selected species in the cat prior to the obesity treatment, wherein if the level of one or more of *Megasphaera elsdenii, Megamonas rupellensis, Megamonas funiformis, Megamonas hypermegale*, and *Bacteroides coprophilus* is increased during treatment, or it the level of one or more of *Lactobacillus reuteri* and *Blautia schinkii* is decreased during treatment, then the treatment is determined to be efficacious.

Disclosed herein are methods of determining if an obesity treatment in a domesticated cat is efficacious, comprising the steps of determining at a time during or following the obesity treatment: (a) if the gut population in the cat of one or more bacterial species selected from *Megasphaera elsdenii, Megamonas rupellensis, Megamonas funiformis, Megamonas hypermegale*, and *Bacteroides coprophilus* is at a level above a pre-determined threshold for the selected bacterial species; and/or (b) if the gut population in the cat of one or more bacterial species selected from *Lactobacillus reuteri* and *Blautia schinkii* is at a level below a pre-determined threshold for the selected bacterial species, thereby determining that the obesity treatment is efficacious.

In some embodiments, the treatment comprises orally administering to the cat an agent that selectively increases the gut population of one or more bacterial species selected from *Megasphaera elsdenii, Megamonas rupellensis, Megamonas funiformis, Megamonas hypermegale*, and *Bacteroides coprophilus*. In some embodiments, the agent comprises mucins. In some embodiments, the treatment comprises orally administering to the cat one or more bacterial species selected from *Megasphaera elsdenii, Megamonas rupellensis, Megamonas funiformis, Megamonas hypermegale,* and *Bacteroides coprophilus.* In some embodiments, the treatment comprises orally administering to the cat an agent which selectively reduces the gut population of one or more bacterial species selected from *Lactobacillus reuteri* and *Blautia schinkii.* In some embodiments, the agent is a lytic bacteriophage specific for *Lactobacillus reuteri* or a lytic bacteriophage specific for *Blautia schinkii.*

In some embodiments, the bacterial species is *Megasphaera elsdenii* strain 14-14 or ATCC-25940. In some embodiments, the bacterial species is *Megamonas hypermegale* strain ART12/1, NCTC10570, DSM-1672T, ABXD-Z48, ABXD-N8, ABXD-L39, or ABXD-AC41. In some embodiments, the bacterial species is *Megamonas rupellensis* strain FM1025. In some embodiments, the bacterial species is *Lactobacillus reuteri* strain 149, JCM-1112, or DSM-20016.

Also disclosed herein are methods of identifying a domesticated cat for obesity or a predisposition to obesity comprising the steps of: (a) measuring the expression of one or more bacterial species in a sample obtained from the domesticated cat, wherein the one or more bacterial species is selected from *Megasphaera elsdenii, Megamonas rupellensis, Megamonas funiformis, Megamonas hypermegale,* and *Bacteroides coprophilus*; and (b) comparing the expression of the one or more bacterial species to a control sample of those bacterial species from domesticated cats without obesity, wherein decreased expression of the one or more bacterial species relative to the control sample is indicative of the domesticated cat being obese or having a predisposition to obesity.

Disclosed herein are methods of identifying a domesticated cat for obesity or a predisposition to obesity comprising the steps of: (a) measuring the expression of one or more bacterial species in a sample obtained from the domesticated cat, wherein the one or more bacterial species is selected from *Lactobacillus reuteri* and *Blautia schinkii*; and (b) comparing the expression of the one or more bacterial species to a control sample of those bacterial species from domesticated cats without obesity, wherein increased expression of the one or more bacterial species relative to the control sample is indicative of the domesticated cat being obese or having a predisposition to obesity.

Also disclosed herein are methods of processing a sample from a domesticated cat suspected of being obese or having a predisposition to obesity comprising the steps of: (a) obtaining a biological sample from a domesticated cat; and (b) measuring the expression of one or more bacterial species, wherein the bacterial species is selected from the group consisting of *Megasphaera elsdenii, Megamonas rupellensis, Megamonas funiformis, Megamonas hypermegale, Bacteroides coprophilus, Lactobacillus reuteri* and *Blautia schinkii.*

Disclosed herein are methods of treating or preventing obesity in a domesticated cat comprising administering a composition comprising one or more bacterial species selected from *Megasphaera elsdenii, Megamonas rupellensis, Megamonas funiformis, Megamonas hypermegale,* and *Bacteroides coprophilus.*

Also disclosed herein are compositions for use in the treatment of obesity in a domesticated cat, wherein the composition comprises one or more bacterial species selected from *Megasphaera elsdenii, Megamonas rupellensis, Megamonas funiformis, Megamonas hypermegale,* and *Bacteroides coprophilus.*

Also disclosed herein are methods of treating obesity in a domesticated dog comprising increasing the population of one or more bacterial species selected from *Eubacterium tenue* and *Clostridium hiranonis* in the gut of the dog to a level over a pre-determined threshold for the selected bacterial species.

Disclosed herein are methods of selecting and treating a domesticated dog for obesity or a predisposition to obesity comprising the steps of: (a) selecting a domesticated dog on the basis of it having a gut population of one or more bacterial species selected from *Eubacterium tenue* and *Clostridium hiranonis* at a level below a pre-determined threshold for the selected bacterial species; and (b) treating the selected dog for obesity.

Also disclosed herein are methods of identifying a domesticated dog for treatment with an anti-obesity agent comprising the step of determining if the dog has a gut population of one or more bacterial species selected from *Eubacterium tenue* and *Clostridium hiranonis* at a level below a pre-determined threshold for the selected bacterial species, thereby identifying the dog for treatment with the anti-obesity agent.

Disclosed herein are methods of diagnosing a domesticated dog for obesity or a predisposition to obesity comprising the step of determining if a gut population of one or more bacterial species selected from *Eubacterium tenue* and *Clostridium hiranonis* in the dog is at a level below a pre-determined threshold for the selected bacterial species, thereby diagnosing the domesticated dog for obesity or a predisposition to obesity.

In some embodiments, the method of diagnosing a domesticated dog for obesity or a predisposition to obesity further comprises the step of treating the dog for obesity if the gut population of one or more bacterial species selected from *Eubacterium tenue* and *Clostridium hiranonis* is at a level below a pre-determined threshold for the selected bacterial species.

Also disclosed herein are methods of determining the efficacy of an obesity treatment in a domesticated dog comprising the steps of: (a) determining at a time during treatment the gut population level of one or more bacterial species selected from *Eubacterium tenue* and *Clostridium hiranonis*; and (b) comparing the determined gut population of the selected bacterial species to a gut population level of the selected species in the dog prior to the obesity treatment, wherein if the level of one or more of *Eubacterium tenue* and *Clostridium hiranonis* is increased during treatment, then the treatment is determined to be efficacious.

Also disclosed herein are methods of determining if an obesity treatment in a domesticated dog is efficacious, comprising the step of determining, at a time during or following the obesity treatment, if the gut population of one or more bacterial species selected from *Eubacterium tenue* and *Clostridium hiranonis* in the dog is at a level above a pre-determined threshold for the selected bacterial species, thereby determining that the obesity treatment is efficacious.

In some embodiments, the treatment comprises orally administering to the dog an agent that selectively increases the gut population of one or more bacterial species selected from *Eubacterium tenue* and *Clostridium hiranonis.* In some embodiments, the agent comprises mucins. In some embodiments, the treatment comprises orally administering to the dog one or more bacterial species selected from *Eubacterium tenue* and *Clostridium hiranonis.*

Also disclosed herein are methods of processing a sample from a domesticated dog suspected of being obese or having a predisposition to obesity comprising the steps of: (a)

obtaining a biological sample from a domesticated dog; and (b) measuring the expression of one or more bacterial species, wherein the bacterial species is selected from the group consisting of *Eubacterium tenue* and *Clostridium hiranonis*.

Disclosed herein are methods of treating or preventing obesity in a domesticated dog comprising administering compositions comprising one or more bacterial species selected from *Eubacterium tenue* and *Clostridium hiranonis*.

Also disclosed herein are compositions for use in the treatment of obesity in a domesticated dog, wherein the composition comprises one or more bacterial species selected from *Eubacterium tenue* and *Clostridium hiranonis*.

Also disclosed herein are methods of screening test agents to identify candidate agents for treating, reducing the likelihood, or preventing obesity in a cat, comprising providing a bacterial culture comprising one or more bacterial species selected from *Megasphaera elsdenii, Megamonas rupellensis, Megamonas funiformis, Megamonas hypermegale*, and *Bacteroides coprophilus*, contacting the culture with the test agents, determining the level of the one or more bacterial species in the contacted culture, and identifying test agents as candidate agents if the contacted culture has an increased level of the one or more bacterial species as compared to a control.

In some embodiments, the bacterial culture further comprises at least one of *Lactobacillus reuteri* and *Blautia schinkii* and the method further comprises determining the level of the at least one of *Lactobacillus reuteri* and *Blautia schinkii* in the contacted culture, and identifying the test agents as candidate agents if the contacted culture has a decreased level of the at least one of *Lactobacillus reuteri* and *Blautia schinkii* as compared to a control. In some embodiments, the culture further comprises mucus (e.g., mucus beads). In some embodiments, the culture is or has been obtained using a cat fecal inoculum.

Also disclosed herein are methods of screening test agents to identify candidate agents for treating, reducing the likelihood, or preventing obesity in a dog, comprising providing a bacterial culture comprising one or more bacterial species selected from *Eubacterium tenue* and *Clostridium hiranonis*, contacting the culture with the one or more test agents, determining the level of the one or more bacterial species in the contacted culture, and identifying the one or more test agents as candidate agents if the contacted culture has a decreased level of the one or more bacterial species as compared to a control.

In some embodiments, the culture further comprises mucus (e.g., mucus beads). In some embodiments, the culture is or has been obtained with a dog fecal sample inoculum.

BRIEF DESCRIPTION OF THE DRAWINGS

FIG. 1 provides a table summarizing sample weight specifications for cats and dogs. The left table provides information regarding domesticated cats that were assessed for microbiome markers. The right table provides information regarding domesticated dogs that were assessed for microbiome markers. Cats and dogs were classified as obese if they had a body condition score (BCS) over 6.5 and were classified as lean if they had a body condition score below 6.5.

FIG. 2A provides screening results for a first experiment examining expression of *L. reuteri* in domesticated cats (8 obese; 8 lean) and FIG. 2B provides screening results when the experiment was repeated. FIGS. 2A-2B show that no lean cats were identified as expressing *L. reuteri* and 7 out of 8 domesticated cats did express it. FIGS. 2C-2D shows that *L. reuteri* is more expressed than other *Lactobacillus* sp. For example, at a lower stringency cut-off, *Lactobacillus salivarious* was detected, but *L. reuteri* was always more expressed than L. salivarious.

FIG. 3A provides screening results for a first experiment examining expression of *B. schinkii* in domesticated cats (8 obese; 8 lean) and FIG. 3B provides the screening results when the experiment was repeated. FIGS. 3A-3B show that, although lean domesticated cats are identified as expressing *B. schinkii*, obese domesticated cats express *B. schinkii* at much higher levels compared to the lean cats. FIG. 3C shows that additional *Blautia* sp. may also exhibit increased expression in obese cats and decreased expression in lean cats.

FIG. 4A provides screening results for a first experiment examining expression of *M. elsdenii* in domesticated cats (8 obese; 8 lean) and FIG. 4B provides the screening results when the experiment was repeated (BESTFIT level at PID>=97). FIGS. 4A-4B show that no obese cats express *M. elsdenii*, while 4 lean cats were identified as expressing *M. elsdenii*. FIG. 4C provides a strain level analysis of *M. elsdenii* and show that not all strains of *M. elsdenii* are equally expressed. In FIG. 4C, strain 14-14 is identified as having the highest levels of expression, identifying it as a possible marker of leanness.

FIG. 5A provides screening results for a first experiment examining expression of *M. rupellensis, M. funiformis*, and *M. hypermegale* in domesticated cats (8 obese; 8 lean) and FIG. 5B provides screening results when the experiment was repeated. FIGS. 5A-5B show that *M. rupellensis, M. funiformis*, and *M. hypermegale* exhibit increased expression in lean cats, while no obese cats expressed any of the three *Megamonas* sp. A strain analysis was also performed, and *M. hypermegale* was identified as strain ART12/1.

FIG. 6A provides screening results for a first experiment examining expression of *B. coprophilus* in domesticated cats (8 obese; 8 lean) and FIG. 6B provides screening results when the experiment was repeated. In the first experiment (FIG. 6A) no expression of *B. coprophilus* was seen in obese cats, while in the second experiment (FIG. 6B) some expression of *B. coprophilus* was seen in obese cats. FIG. 6B 16S Petseq Species ID Bestfit level at PID>=99. Nonetheless, overall there is clearly higher expression of *B. Coprophilus* in lean cats than in obese cats.

FIG. 7A provides screening results for a first experiment examining expression of *E. tenue* and *C. hiranonis* in domesticated dogs (10 obese; 10 lean) and FIG. 7B provides screening results when the experiment was repeated. Although some expression of both *E. tenue* and *C. hiranonis* was found in obese dogs, expression levels were clearly high in lean dogs.

FIG. 8A provides confirmation of screening results showing obese animals have decreased levels of *Megasphaera elsdenii* and *Megamonas hypermegale*, both markers of leanness, as well as showing obese animals have increased levels of *Lactobacillus reuteri*, a marker of obesity. FIG. 8B shows *M. hypermegale* strains are detected only in lean animals (confirming species-specific results) and are differentially expressed. FIG. 8C shows *M. elsdenii* strains are detected only in lean animals (confirming species-specific results) and are differentially expressed. FIG. 8D shows *L. reuteri* strains are detected only in obese animals (confirming species-specific results) and are differentially expressed.

FIG. 9A shows qPCR validation of the screening results of *M. hypermegale*. Four different cats were tested (Samples 1-4) and each cat has lean and obese samples (LC1-4 and OC1-4). FIG. 9B shows qPCR validation of the screening results of *L. reuteri*. Two different cats were tested (Samples 1 and 2) and each cat has lean and obese samples (LC1, LC2, OC1, and OC2).

FIGS. 10A-10B demonstrate strain specific analysis of the various bacterial species. FIG. 10A summarizes the sample details for the strain specific analysis. FIG. 10B provides the results of the strain specific analysis, which identifies specific bacterial strains of interest.

DETAILED DESCRIPTION OF THE INVENTION

Figures 2A, 2B:
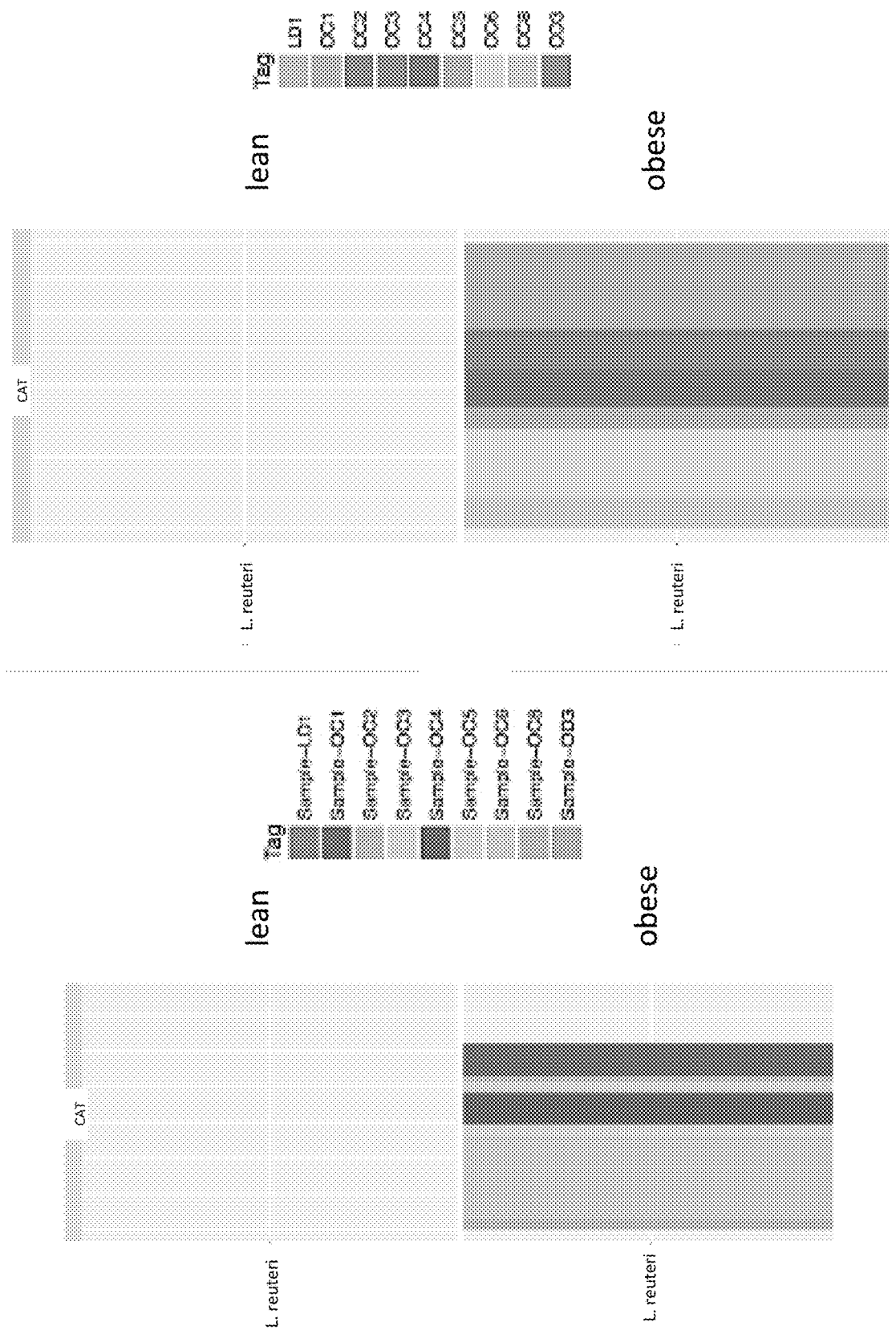
FIGS. 2A-2D demonstrate *Lactobacillus reuteri* as a possible marker of obesity in domesticated cats.

Aspects of the disclosure relate to identifying specific bacterial species that may be used as biomarkers for obesity or leanness. The identified biomarkers may be used for diagnostic and therapeutic purposes.

Disclosed herein are biomarkers for obesity or leanness of domesticated cats and dogs. Obese domesticated cats are cats identified as having a body condition score (BCS) of 6.5 or above and lean domesticated cats are cats identified as having a BCS of below 6.5. Obese domesticated dogs are dogs identified as having a BCS above 6.5 and lean domesticated dogs are dogs identified as having a BCS below 6.5. Dogs identified as having a BCS of 6.5 may be classified as either lean or obese. Bacterial species that may exhibit increased expression in obese domesticated cats include *Lactobacillus reuteri* and *Blautia schinkii*. Bacterial species that may exhibit increased expression in lean domesticated cats include *Megasphaera elsdenii, Megamonas rupellensis, Megamonas funiformis, Megamonas hypermegale*, and *Bacteroides* coprophilous. Bacterial species that may exhibit increased expression in lean domesticated dogs include *Eubacterium tenue* and *Clostridium hiranonis*.

In some aspects an obese cat exhibits increased expression of *Lactobacillus reuteri*. In some aspects a lean cat exhibits decreased expression of *Lactobacillus reuteri*. The strain of *L. reuteri* may be strain I49, JCM-1112, and/or DSM-20016. In some aspects an obese cat exhibits increased expression of *Blautia schinkii*. In some aspects a lean cat exhibits decreased expression of *Blautia schinkii*. In some aspects an obese cat exhibits decreased expression of *Megasphaera elsdenii*. In some aspects a lean cat exhibits increased expression of *Megasphaera elsdenii*. The strain of *M. elsdenii* may be strain ATCC-25940 and/or 14-14. In some aspects an obese cat exhibits decreased expression of *Megamonas rupellensis*. In some aspects a lean cat exhibits increased expression of *Megamonas rupellensis*. The strain of *M. rupellensis* may be strain FM1025. In some aspects an obese cat exhibits decreased expression of *Megamonas funiformis*. In some aspects a lean cat exhibits increased expression of *Megamonas funiformis*. In some aspects an obese cat exhibits decreased expression of *Megamonas hypermegale*. In some aspects a lean cat exhibits increased expression of *Megamonas hypermegale*. The strain of *M. hypermegale* may be strain ART12/1, NCTC10570, DSM-1672T, ABXD-Z48, ABXD-N8, ABXD-L39, and/or ABXD-AC41. In some aspects an obese cat exhibits decreased expression of *Bacteroides* coprophilous. In some aspects a lean cat exhibits increased expression of *Bacteroides* coprophilous.

Generally disclosed herein are methods for diagnosing a disease (e.g., obesity) based on the levels of one or more biomarkers. Methods of diagnosing or identifying a domesticated cat or dog for obesity or a predisposition to obesity are disclosed herein. Also disclosed herein are methods of identifying a domesticated cat or dog for treatment with an anti-obesity agent. In some embodiments the methods comprise determining if a domesticated cat or dog has one or more bacterial species above a pre-determined threshold. In some embodiments the methods comprise determining if a domesticated cat or dog has one or more bacterial species below a pre-determined threshold.

A "pre-determined threshold" as used herein refers to a quantitative threshold value or range for a selected bacterial species. The threshold value provides a point or range at which a bacterial species acts as a biomarker for obesity or leanness. A pre-determined threshold level may be a fixed value or a value range for each individual bacterial species (e.g., unique pre-determined threshold values for *Megasphaera elsdenii, Megamonas rupellensis, Megamonas funiformis, Megamonas hypermegale, Bacteroides coprophilous, Lactobacillus reuteri Blautia schinkii, Eubacterium tenue* and *Clostridium hiranonis*). In some aspects a pre-determined threshold value may be calculated by measuring the expression level or DNA copy number presence of a specific bacterial species from a control sample obtained from a domesticated cat or dog (e.g., a domesticated cat or dog that does not qualify as lean or obese). In some aspects a pre-determined threshold value may be calculated by measuring the expression level or DNA copy number presence of a specific bacterial species from a control sample obtained from the average of a group (e.g., 5 or more, 10 or more, 20 or more, etc.) of domesticated cats or dogs (e.g., domesticated cats or dogs that do not qualify as lean or obese).

As used herein, a "reduced level" of expression or activity is a level of expression or activity that is detectably lower than a pre-determined threshold or reference level. In some embodiments, a reduced level of expression or activity is between 10% and 95% of a pre-determined threshold, although lesser and greater reductions are contemplated in some embodiments. In some embodiments expression or activity is reduced by about 75%, about 80%, about 85%, about 90%, about 95%, about 98%, or about 100%. In some embodiments a reduced level of expression or activity is between 0% and 5% of a pre-determined threshold. In some embodiments a reduced level of expression or activity is between 5% and 15% of a pre-determined threshold. In some embodiments a reduced level of expression or activity is between 15% and 95%, e.g., between 20% and 80%, between 25% and 75%, between 30% and 70%, or between 40% and 60% of a pre-determined threshold. In some embodiments a reduced level of expression or activity is between 25% and 50% or between 50% and 75% of a pre-determined threshold. In some embodiments a reduced level of expression or activity is about 1%, about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99% or about 100% of a pre-determined threshold (but less than the pre-determined threshold).

As used herein, an "increased level" of expression or activity is a level of expression or activity that is detectably higher than a pre-determined threshold. In some embodiments, an increased level of expression or activity is between 10% and 100% above a pre-determined threshold, although lesser and greater increases are contemplated in some embodiments. In some embodiments an increased level of expression or activity is between 15% and 95%, e.g., between 20% and 80%, between 25% and 75%, between 30% and 70%, or between 40% and 60% above a pre-determined threshold. In some embodiments an increased level of expression or activity is between 25% and 50% or between 50% and 75% above a pre-determined threshold. In some embodiments an increased level of expression or activity is about 10%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99% or about 100% above a pre-determined threshold. In some embodiments an increased level of expression or activity is increased over a pre-determined threshold by a factor of at least 2-fold, at least 3-fold, at least 4-fold, at least 5-fold, at least 6-fold, at least 7-fold, at least 8-fold, at least 9-fold, or at least 10-fold.

In some embodiments the methods comprise determining if a domesticated cat has a gut population of one or more bacterial species selected from *Megasphaera elsdenii*, *Megamonas rupellensis*, *Megamonas funiformis*, *Megamonas hypermegale*, and *Bacteroides* coprophilous at a level below a pre-determined threshold (e.g., a pre-determined threshold for the selected bacterial species). In some aspects the one or more bacterial species are characterized as being between 15% and 95%, e.g., between 20% and 80%, between 25% and 75%, between 30% and 70%, or between 40% and 60% below a pre-determined threshold for the selected bacterial species. In some aspects the methods comprise determining if a domesticated cat has a gut population of one, two, three, four, or five bacterial species selected from *Megasphaera elsdenii*, *Megamonas rupellensis*, *Megamonas funiformis*, *Megamonas hypermegale*, and *Bacteroides* coprophilous at a level below a pre-determined threshold (e.g., a pre-determined threshold for the selected bacterial species). In some aspects the methods comprise determining if a domesticated cat has a gut population of *Megasphaera elsdenii* at a level below a pre-determined threshold. In certain aspects the bacterial strain of *Megasphaera elsdenii* is strain 14-14. In certain aspects the bacterial strain of *Megasphaera elsdenii* is strain ATCC-25940. In some aspects the methods comprise determining if a domesticated cat has a gut population of *Megamonas rupellensis* at a level below a pre-determined threshold. In certain aspects the bacterial strain of *Megamonas rupellensis* is strain FM1025. In some aspects the methods comprise determining if a domesticated cat has a gut population of *Megamonas funiformis* at a level below a pre-determined threshold. In some aspects the methods comprise determining if a domesticated cat has a gut population of *Megamonas hypermegale* at a level below a pre-determined threshold. In certain aspects the bacterial strain of *Megamonas hypermegale* is strain ART12/1. In certain aspects the bacterial strain of *Megamonas hypermegale* is strain NCTC10570. In certain aspects the bacterial strain of *Megamonas hypermegale* is strain DSM-1672T. In certain aspects the bacterial strain of *Megamonas hypermegale* is strain ABXD-Z48. In certain aspects the bacterial strain of *Megamonas hypermegale* is strain ABXD-N8. In certain aspects the bacterial strain of *Megamonas hypermegale* is strain ABXD-L39. In certain aspects the bacterial strain of *Megamonas hypermegale* is strain ABXD-AC41. In some aspects the methods comprise determining if a domesticated cat has a gut population of *Bacteroides* coprophilous at a level below a pre-determined threshold.

In some embodiments the methods comprise determining if a domesticated cat has a gut population of one or more bacterial species selected from *Lactobacillus reuteri* and *Blautia schinkii* at a level above a pre-determined threshold (e.g., a pre-determined threshold for the selected bacterial species). In some aspects the one or more bacterial species are characterized as being between 15% and 95%, e.g., between 20% and 80%, between 25% and 75%, between 30% and 70%, or between 40% and 60% above a pre-determined threshold for the selected bacterial species. In some aspects the one or more bacterial species are characterized as being at least 2-fold, at least 3-fold, at least 4-fold, at least 5-fold above a pre-determined threshold for the selected bacterial species. In some aspects the methods comprise determining if a domesticated cat has a gut population of one or two bacterial species selected from *Lactobacillus reuteri* and *Blautia schinkii* at a level above a pre-determined threshold (e.g., a pre-determined threshold for the selected bacterial species). In some aspects the methods comprise determining if a domesticated cat has a gut population of *Lactobacillus reuteri* at a level above a pre-determined threshold. In certain aspects the bacterial strain of *Lactobacillus reuteri* is strain I49. In certain aspects the bacterial strain of *Lactobacillus reuteri* is strain JCM-1112. In certain aspects the bacterial strain of *Lactobacillus reuteri* is strain DSM-20016. In some aspects the methods comprise determining if a domesticated cat has a gut population of *Blautia schinkii* at a level above a pre-determined threshold.

In some embodiments the methods comprise determining if a domesticated dog has a gut population of one or more bacterial species selected from *Eubacterium tenue* and *Clostridium hiranonis* at a level below a pre-determined threshold (e.g., a pre-determined threshold for the selected bacterial species).). In some aspects the one or more bacterial species are characterized as being between 15% and 95%, e.g., between 20% and 80%, between 25% and 75%, between 30% and 70%, or between 40% and 60% below a pre-determined threshold for the selected bacterial species. In some aspects the methods comprise determining if a domesticated dog has a gut population of one or two bacterial species selected from *Eubacterium tenue* and *Clostridium hiranonis* at a level below a pre-determined threshold (e.g., a pre-determined threshold for the selected bacterial species). In some aspects the methods comprise determining if a domesticated dog has a gut population of *Eubacterium tenue* at a level below a pre-determined threshold. In some aspects the methods comprise determining if a domesticated dog has a gut population of *Clostridium hiranonis* at a level below a pre-determined threshold.

In some embodiments a method of identifying a domesticated cat or dog for obesity or a predisposition to obesity includes measuring the expression (i.e., level) of one or more bacterial species in a sample obtained from a domesticated cat or dog and comparing the expression of the one or more bacterial species to a control sample. In some aspects the sample is obtained from a cat and the one or more bacterial species are selected from *Megasphaera elsdenii, Megamonas rupellensis, Megamonas funiformis, Megamonas hypermegale*, and *Bacteroides coprophilous*. In some aspects the sample is obtained from a cat and the one, two, three, four, or five bacterial species are selected from *Megasphaera elsdenii, Megamonas rupellensis, Megamonas funiformis, Megamonas hypermegale*, and *Bacteroides coprophilous*. In some aspects the expression of the one or more bacterial species is compared to a control sample. The control sample may be obtained from a non-obese domesticated cat (e.g., a cat with a body condition score below 6.5). In some aspects decreased expression of the one or more bacterial species relative to the control sample is indicative of the domesticated cat being obese or having a predisposition to obesity. In some aspects the one or more bacterial species are characterized as having decreased expression between 15% and 95%, e.g., between 20% and 80%, between 25% and 75%, between 30% and 70%, or between 40% and 60% of a control sample for the selected bacterial species.

In some aspects the sample is obtained from a cat and the one or more bacterial species are selected from *Lactobacillus reuteri* and *Blautia schinkii*. In some aspects the sample is obtained from a cat and the one or two bacterial species are selected from *Lactobacillus reuteri* and *Blautia schinkii*. In some aspects the expression of the one or more bacterial species is compared to a control sample. The control sample may be obtained from a non-obese domesticated cat (e.g., a cat with a body condition score below 6.5) or may be the average level in samples from a group (e.g., 5 or more, 10 or more, 20 or more, etc.) of non-obese domesticated cats. In some aspects increased expression of the one or more bacterial species relative to the control sample is indicative of the domesticated cat being obese or having a predisposition to obesity. In some aspects the one or more bacterial species are characterized as having increased expression between 15% and 95%, e.g., between 20% and 80%, between 25% and 75%, between 30% and 70%, or between 40% and 60% of a control sample for the selected bacterial species. In some aspects the one or more bacterial species are characterized as having increased expression at least 2-fold, at least 3-fold, at least 4-fold, or at least 5-fold above a control sample for the selected bacterial species In some aspects the sample is obtained from a dog and the one or more bacterial species are selected from *Eubacterium tenue* and *Clostridium hiranonis*. In some aspects the sample is obtained from a dog and the one or two bacterial species are selected from *Eubacterium tenue* and *Clostridium hiranonis*. In some aspects the expression of the one or more bacterial species is compared to a control sample. The control sample may be obtained from a non-obese domesticated dog (e.g., a dog with a body condition score below 6.5). In some aspects decreased expression of the one or more bacterial species relative to the control sample is indicative of the domesticated dog being obese or having a predisposition to obesity. In some aspects the one or more bacterial species are characterized as having decreased expression between 15% and 95%, e.g., between 20% and 80%, between 25% and 75%, between 30% and 70%, or between 40% and 60% of a control sample for the selected bacterial species.

Also disclosed herein are methods of processing samples obtained from domesticated cats and/or dogs suspected of being obese or having a predisposition to obesity. In some embodiments the methods comprise obtaining a biological sample from a domesticated cat or dog and measuring the expression of one or more bacterial species. In some aspects the methods comprise obtaining a biological sample from a domesticated cat and measuring the expression of one or more bacterial species selected from *Megasphaera elsdenii, Megamonas rupellensis, Megamonas funiformis, Megamonas hypermegale, Bacteroides coprophilousi, Lactobacillus reuteri* and *Blautia schinkii*. In some aspects the methods comprise obtaining a biological sample from a domesticated dog and measuring the expression of one or more bacterial species selected from *Eubacterium tenue* and *Clostridium hiranonis*.

Also disclosed herein are methods for identifying or selecting a cat or dog for treatment of obesity or a predisposition to obesity. In some embodiments a cat is selected for treatment on the basis of the cat having a gut population of one or more bacterial species (e.g., one, two, three, four, or five bacterial species) selected from *Megasphaera elsdenii, Megamonas rupellensis, Megamonas funiformis, Megamonas hypermegale*, and *Bacteroides coprophilous* at a level below a pre-determined threshold (e.g., a pre-determined threshold for the selected bacterial species). In some embodiments a cat is selected for treatment on the basis of the cat having a gut population of one or more bacterial species (e.g., one or two bacterial species) selected from *Lactobacillus reuteri* and *Blautia schinkii* at a level above a pre-determined threshold (e.g., a pre-determined threshold for the selected bacterial species). In some embodiments a cat selected for treatment of obesity or a predisposition to obesity is treated by one of the methods described herein.

In some embodiments a dog is selected for treatment on the basis of the dog having a gut population of one or more bacterial species (e.g., one or two) selected from *Eubacterium tenue* and *Clostridium hiranonis* at a level below a pre-determined threshold (e.g., a pre-determined threshold for the selected bacterial species). In some embodiments a dog selected for treatment of obesity or a predisposition to obesity is treated by one of the methods described herein.

Disclosed herein are methods for treating obesity or a predisposition to obesity in a domesticated cat or dog. In some embodiments the methods comprise increasing the population of one or more bacterial species selected from *Megasphaera elsdenii, Megamonas rupellensis, Megamonas funiformis, Megamonas hypermegale*, and *Bacteroides coprophilous* in the gut of a cat to a level over a pre-determined threshold (e.g., a pre-determined threshold for the selected bacterial species). In some embodiments the methods comprise increasing the population of one, two, three, four, or five bacterial species selected from *Megasphaera elsdenii, Megamonas rupellensis, Megamonas funiformis, Megamonas hypermegale*, and *Bacteroides coprophilous* in the gut of a cat to a level over a pre-determined threshold (e.g., a pre-determined threshold for the selected bacterial species). In some aspects the methods comprise increasing the population of *Megasphaera elsdenii* in the gut of a cat to a level over a pre-determined threshold. In certain aspects the bacterial strain of *Megasphaera elsdenii* is strain 14-14. In certain aspects the bacterial strain of *Megasphaera elsdenii* is strain ATCC-25940. In some aspects the methods comprise increasing the population of

*Megamonas rupellensis* in the gut of a cat to a level over a pre-determined threshold. In certain aspects the bacterial strain of *Megamonas rupellensis* is strain FM1025. In some aspects the methods comprise increasing the population of *Megamonas funiformis* in the gut of a cat to a level over a pre-determined threshold. In some aspects the methods comprise increasing the population of *Megamonas hypermegale* in the gut of a cat to a level over a pre-determined threshold. In certain aspects the bacterial strain of *Megamonas hypermegale* is strain ART12/1. In certain aspects the bacterial strain of *Megamonas hypermegale* is strain NCTC10570. In certain aspects the bacterial strain of *Megamonas hypermegale* is strain DSM-1672T. In certain aspects the bacterial strain of *Megamonas hypermegale* is strain ABXD-Z48. In certain aspects the bacterial strain of *Megamonas hypermegale* is strain ABXD-N8. In certain aspects the bacterial strain of *Megamonas hypermegale* is strain ABXD-L39. In certain aspects the bacterial strain of *Megamonas hypermegale* is strain ABXD-AC41. In some aspects the methods comprise increasing the population of *Bacteroides coprophilous* in the gut of a cat to a level over a pre-determined threshold.

In some embodiments the methods comprise decreasing the population of one or more bacterial species selected from *Lactobacillus reuteri* and *Blautia schinkii* in the gut of a cat to a level below a pre-determined threshold (e.g., a pre-determined threshold for the selected bacterial species). In some embodiments the methods comprise decreasing the population of one or two bacterial species selected from *Lactobacillus reuteri* and *Blautia schinkii* in the gut of a cat to a level below a pre-determined threshold (e.g., a pre-determined threshold for the selected bacterial species). In some aspects the methods comprise decreasing the population of *Lactobacillus reuteri* in the gut of a cat to a level below a pre-determined threshold. In certain aspects the bacterial strain of *Lactobacillus reuteri* is strain I49. In certain aspects the bacterial strain of *Lactobacillus reuteri* is strain JCM-1112. In certain aspects the bacterial strain of *Lactobacillus reuteri* is strain DSM-20016. In some aspects the methods comprise decreasing the population of *Blautia schinkii* in the gut of a cat to a level below a pre-determined threshold.

In some embodiments the methods comprise increasing the population of one or more bacterial species selected from *Eubacterium tenue* and *Clostridium hiranonis* in the gut of a dog to a level above a pre-determined threshold (e.g., a pre-determined threshold for the selected bacterial species). In some embodiments the methods comprise increasing the population of one or two bacterial species selected from *Eubacterium tenue* and *Clostridium hiranonis* in the gut of a dog to a level above a pre-determined threshold (e.g., a pre-determined threshold for the selected bacterial species). In some aspects the methods comprise increase the population of *Eubacterium tenue* in the gut of a dog to a level above a pre-determined threshold. In some aspects the methods comprise increasing the population of *Clostridium hiranonis* in the gut of a dog to a level above a pre-determined threshold.

In some embodiments treating obesity or a predisposition to obesity in a domesticated cat or dog comprises orally administering to the cat or dog an agent. In some aspects the agent selectively increases the gut population of one or more bacterial species. In other aspects the agent selectively decreases or reduces the gut population of one or more bacterial species.

In some aspects an agent administered to a cat selectively increases the gut population of one or more (e.g., one, two, three, four, or five) bacterial species selected from *Megasphaera elsdenii, Megamonas rupellensis, Megamonas funiformis, Megamonas hypermegale,* and *Bacteroides coprophilous*. In some aspects an agent administered to a cat selectively increases the gut population of *Megasphaera elsdenii*. In some aspects an agent administered to a cat selectively increases the gut population of *Megamonas rupellensis*. In some aspects an agent administered to a cat selectively increases the gut population of *Megamonas funiformis*. In some aspects an agent administered to a cat selectively increases the gut population of *Megamonas hypermegale*. In some aspects an agent administered to a cat selectively increases the gut population of *Bacteroides coprophilous*.

In some embodiments, the agent comprises mucins. The source of mucins is not limited. In some embodiments, the mucins comprise chicken mucins. In some embodiments, the mucins comprise porcine mucins. In some embodiments, the porcine mucins are obtained from porcine gastrointestinal tract. In some embodiments, the agent (e.g., mucins) comprises less than 1% free glycans.

In some aspects an agent administered to a cat selectively decreases or reduces the gut population of one or more (e.g., one or two) bacterial species selected from *Lactobacillus reuteri* and *Blautia schinkii*. In some aspects an agent administered to a cat selectively reduces the gut population of *Lactobacillus reuteri*. In some aspects an agent administered to a cat selectively reduces the gut population of *Blautia schinkii*. In some aspects an agent is a lytic bacteriophage specific for *Lactobacillus reuteri* and/or a lytic bacteriophage specific for *Blautia schinkii*.

In some aspects an agent administered to a dog selectively increases the gut population of one or more (e.g., one or two) bacterial species selected from *Eubacterium tenue* and *Clostridium hiranonis*. In some aspects an agent administered to a dog selectively increases the gut population of *Eubacterium tenue*. In some aspects an agent administered to a dog selectively increases the gut population of *Clostridium hiranonis*.

In some embodiments, the agent comprises mucins. The source of mucins is not limited. In some embodiments, the mucins comprise chicken mucins. In some embodiments, the mucins comprise porcine mucins. In some embodiments, the porcine mucins are obtained from porcine gastrointestinal tract. In some embodiments, the agent (e.g., mucins) comprises less than 1% free glycans.

In some embodiments treating obesity or a predisposition to obesity in a domesticated cat or dog comprises orally administering to the cat or dog one or more bacterial species. In some aspects a cat is orally administered one or more (e.g., one, two, three, four, or five) bacterial species selected from *Megasphaera elsdenii, Megamonas rupellensis, Megamonas funiformis, Megamonas hypermegale,* and *Bacteroides coprophilous*. In some aspects a cat is orally administered *Megasphaera elsdenii*. In some aspects a cat is orally administered *Megamonas rupellensis*. In some aspects a cat is orally administered *Megamonas funiformis*. In some aspects a cat is orally administered *Megamonas hypermegale*. In some aspects a cat is orally administered *Bacteroides coprophilous*. In some aspects a dog is orally administered one or more (e.g., one or two) bacterial species selected from *Eubacterium tenue* and *Clostridium hiranonis*. In some aspects a dog is orally administered *Eubacterium tenue*. In some aspects a dog is orally administered *Clostridium hiranonis*.

In some aspects a composition for use in the treatment of obesity in a domesticated cat or dog comprises one or more bacterial species. In some aspects a composition for use in the treatment of obesity in a domesticated cat comprises one or more (e.g., one, two, three, four, or five) bacterial species selected from *Megasphaera elsdenii, Megamonas rupellensis, Megamonas funiformis, Megamonas hypermegale*, and *Bacteroides* coprophilous. In some aspects a composition for use in the treatment of obesity in a domesticated cat comprises *Megasphaera elsdenii*. In some aspects a composition for use in the treatment of obesity in a domesticated cat comprises *Megamonas rupellensis*. In some aspects a composition for use in the treatment of obesity in a domesticated cat comprises *Megamonas funiformis*. In some aspects a composition for use in the treatment of obesity in a domesticated cat comprises *Megamonas hypermegale*. In some aspects a composition for use in the treatment of obesity in a domesticated cat comprises *Bacteroides* coprophilous. In some aspects a composition for use in the treatment of obesity in a domesticated dog comprises one or more (e.g., one or two) bacterial species selected from *Eubacterium tenue* and *Clostridium hiranonis*. In some aspects a composition for use in the treatment of obesity in a domesticated dog comprises *Eubacterium tenue*. In some aspects a composition for use in the treatment of obesity in a domesticated dog comprises *Clostridium hiranonis*.

In some embodiments treatment of obesity or a predisposition to obesity in a domesticated cat or dog includes modifying the diet of the cat or dog (e.g., modifying amount of food, type of food, number of meals a day, and the like) and/or modifying the amount of exercise the cat or dog is receiving (e.g., increase duration of exercise or number of times the cat or dog exercises). In some embodiments treatment of obesity or a predisposition to obesity in domesticated cat or dog includes treating the cat or dog with a prebiotic, mucins (e.g., mucins as described herein), glycans, a probiotic, or any other dietary aid known to those of ordinary skill. It is generally understood that a cat or dog identified as being obese or having a predisposition to obesity may be treated using one or more of the described methods for treatment, and these methods may be combined with obesity treatments known to those of skill in the art.

Also disclosed herein are methods of determining the efficacy of an obesity treatment in a domesticated cat or dog. In some embodiments, methods of determining if an obesity treatment in a domesticated cat is efficacious comprises determining at a time during or following the obesity treatment if the gut population in the cat or dog of one or more bacterial species is at a level above or below a pre-determined threshold, thereby determining that the obesity treatment is efficacious. In some aspects the method comprises determining if the gut population in a cat of one or more (e.g., one, two, three, four, or five) bacterial species selected from *Megasphaera elsdenii, Megamonas rupellensis, Megamonas funiformis, Megamonas hypermegale*, and *Bacteroides* coprophilousi is at a level above a pre-determined threshold (e.g., a pre-determined threshold for the selected bacterial species). In some aspects the method comprises determining if the gut population in a cat of *Megasphaera elsdenii* is at a level above a pre-determined threshold. In some aspects the method comprises determining if the gut population in a cat of *Megamonas rupellensis* is at a level above a pre-determined threshold. In some aspects the method comprises determining if the gut population in a cat of *Megamonas funiformis* is at a level above a pre-determined threshold. In some aspects the method comprises determining if the gut population in a cat of *Megamonas hypermegale* is at a level above a pre-determined threshold. In some aspects the method comprises determining if the gut population in a cat of *Bacteroides* coprophilousi is at a level above a pre-determined threshold.

In some aspects the method comprises determining if the gut population in a cat of one or more (e.g., one or two) bacterial species selected from *Lactobacillus reuteri* and *Blautia schinkii* is at a level below a pre-determined threshold (e.g., a pre-determined threshold for the selected bacterial species). In some aspects the method comprises determining if the gut population in a cat of *Lactobacillus reuteri* is at a level below a pre-determined threshold. In some aspects the method comprises determining if the gut population in a cat of *Blautia schinkii* is at a level below a pre-determined threshold.

In some aspects the method comprises determining if the gut population in a dog of one or more (e.g., one or two) bacterial species selected from *Eubacterium tenue* and *Clostridium hiranonis* is at a level above a pre-determined threshold (e.g., a pre-determined threshold for the selected bacterial species). In some aspects the method comprises determining if the gut population in a dog of *Eubacterium tenue* is at a level above a pre-determined threshold. In some aspects the method comprises determining if the gut population in a dog of *Clostridium hiranonis* is at a level above a pre-determined threshold.

In some embodiments a method of determining the efficacy of an obesity treatment in a domesticated cat or dog comprises determining at a time during treatment one or more of the gut population level of one or more bacterial species and comparing the determined gut population of the selected bacterial species to a gut population level of the selected species in the cat or dog prior to the obesity treatment. In some embodiments, the one or more (e.g., one, two, three, four, or five) bacterial species are selected from *Megasphaera elsdenii, Megamonas rupellensis, Megamonas funiformis, Megamonas hypermegale*, and *Bacteroides* coprophilousi in a cat. If the level of one or more of *Megasphaera elsdenii, Megamonas rupellensis, Megamonas funiformis, Megamonas hypermegale*, and *Bacteroides* coprophilousi is increased during treatment, then the treatment is determined to be efficacious. In some embodiments, the one or more (e.g., one or two) bacterial species are selected from *Lactobacillus reuteri* and *Blautia schinkii* in a cat. If the level of one or more of *Lactobacillus reuteri* and *Blautia schinkii* is decreased during treatment, then the treatment is determined to be efficacious. In some embodiments, the one or more (e.g., one or two) bacterial species are selected from *Eubacterium tenue* and *Clostridium hiranonis* in a dog. If the level of one or more of *Eubacterium tenue* and *Clostridium hiranonis* is increased during treatment, then the treatment is determined to be efficacious.

As used herein "treatment" or "treating", in reference to a subject (e.g., a domesticated cat or dog), includes amelioration, cure, and/or maintenance of a cure (i.e., the prevention or delay of relapse and/or reducing the likelihood of recurrence) of a disorder (e.g., obesity). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). Treating encompasses administration of an agent that may not have an effect on the disorder by itself but increases the efficacy of a second agent administered to the subject. A suitable dose and therapeutic regimen may vary depending upon the specific agent used, the mode of delivery of the compound, and whether it is used alone or in combination.

As used herein, in the context of treatment of obesity, a therapeutically effective amount generally refers to an amount of an agent or composition that inhibits weight gain and/or enhances the ability of a second agent or composition to inhibit weight gain. In some embodiments, a therapeutically effective amount is an amount of an agent or composition sufficient to inhibit weight gain or cause weight loss. A therapeutically effective amount can refer to any one or more of the agents or compositions described herein, or discovered using the methods described herein, that limit weight gain or contribute to weight loss.

The dosage, administration schedule and method of administering the agent or bacterial species are not limited. In certain embodiments a reduced dose may be used when two or more agents are administered in combination either concomitantly or sequentially. The absolute amount will depend upon a variety of factors including other treatment(s), the number of doses and the individual subject parameters including age, physical condition, size and weight. These are factors well known to those of ordinary skill in the art and can be addressed with no more than routine experimentation. In some embodiments, a maximum tolerated dose may be used, that is, the highest safe and tolerable dose according to sound medical judgment.

As used herein, pharmaceutical compositions comprise one or more agents or bacterial species that have therapeutic utility, and a pharmaceutically acceptable carrier, e.g., a carrier that facilitates delivery of agents or compositions. Agents and pharmaceutical compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, dermally, or as an aerosol. Depending upon the type of condition (e.g., obesity) to be treated, compounds of the invention may, for example, be inhaled, ingested or administered by systemic routes. Thus, a variety of administration modes, or routes, are available. The particular mode selected will typically depend on factors such as the particular compound selected, the particular condition being treated and the dosage required for therapeutic efficacy. The methods described herein, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. Other appropriate routes will be apparent to one of ordinary skill in the art.

Some aspects of the invention are directed to a composition comprising an agent or bacterial species identified by the methods described herein. In some embodiments, the composition further comprises an anti-obesity agent.

In addition to the active agent(s), the pharmaceutical compositions typically comprise a pharmaceutically-acceptable carrier. The term "pharmaceutically-acceptable carrier", as used herein, means one or more compatible solid or liquid vehicles, fillers, diluents, or encapsulating substances which are suitable for administration to a domesticated cat or dog. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically-acceptable carriers should be of sufficiently high purity and sufficiently low toxicity to render them suitable for administration to the human or non-human animal being treated.

Some examples of substances which can serve as pharmaceutically-acceptable carriers are pyrogen-free water; isotonic saline; phosphate buffer solutions; sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

A pharmaceutically-acceptable carrier employed in conjunction with the compounds described herein is used at a concentration or amount sufficient to provide a practical size to dosage relationship. The pharmaceutically-acceptable carriers, in total, may, for example, comprise from about 60% to about 99.99999% by weight of the pharmaceutical compositions, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof in certain embodiments. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that a compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The agents may be administered in pharmaceutically acceptable solutions, which may routinely contain pharmaceutically acceptable concentrations of salt, buffering agents, preservatives, compatible carriers, adjuvants, and optionally other therapeutic ingredients.

The agents may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Generally, treatment of a subject can include a single treatment or, in many cases, can include a series of treatments. A pharmaceutical composition can be administered at various intervals and over different periods of time as required, e.g., multiple times per day, daily, every other day, once or more a week for between about 1 to 10 weeks, between 2 to 8 weeks, between about 3 to 7 weeks, about 4, 5, or 6 weeks, etc. It will be appreciated that multiple cycles of administration may be performed. Numerous variations are possible. The skilled artisan will appreciate that certain factors can influence the dosage and timing required to effectively treat a subject, including but not limited to the severity of the disease or disorder, previous treatments, the general health and/or age of the subject, and other diseases present.

Some aspects of the present invention are directed to methods of screening test agents to identify candidate agents for treating, reducing the likelihood, or preventing obesity in a cat, comprising providing a bacterial culture comprising one or more bacterial species selected from *Megasphaera elsdenii*, *Megamonas rupellensis*, *Megamonas funiformis*, *Megamonas hypermegale*, and *Bacteroides coprophilus*, contacting the culture with the test agents, determining the level of the one or more bacterial species in the contacted culture, and identifying test agents as candidate agents if the contacted culture has an increased level of the one or more bacterial species as compared to a control.

In some embodiments, the bacterial culture further comprises at least one of *Lactobacillus reuteri* and *Blautia schinkii* and the method further comprises determining the level of the at least one of *Lactobacillus reuteri* and *Blautia schinkii* in the contacted culture, and identifying the test agents as candidate agents if the contacted culture has a decreased level of the at least one of *Lactobacillus reuteri* and *Blautia schinkii* as compared to a control. In some embodiments, the culture further comprises mucus (e.g., mucus beads). In some embodiments, the culture is or has been obtained using a cat fecal inoculum.

In some embodiments, the *Megasphaera elsdenii* comprises *Megasphaera elsdenii* strain 14-14. In some embodiments, the *Megasphaera elsdenii* comprises *Megasphaera elsdenii* strain ATCC-25940. In some embodiments, the *Megamonas hypermegale* comprises *Megamonas hypermegale* strain ART12/1. In some embodiments, the *Megamonas hypermegale* comprises *Megamonas hypermegale* strain NCTC10570. In some embodiments, the *Megamonas hypermegale* comprises *Megamonas hypermegale* strain DSM-1672T. In some embodiments, the *Megamonas hypermegale* comprises *Megamonas hypermegale* strain ABXD-Z48. In some embodiments, the *Megamonas hypermegale* comprises *Megamonas hypermegale* strain ABXD-N8. In some embodiments, the *Megamonas hypermegale* comprises *Megamonas hypermegale* strain ABXD-L39. In some embodiments, the *Megamonas hypermegale* comprises *Megamonas hypermegale* strain ABXD-AC41. In some embodiments, the *Megamonas rupellensis* comprises *Megamonas rupellensis* strain FM1025. In some embodiments, the *Lactobacillus reuteri* comprises *Lactobacillus reuteri* strain JCM-1112. In some embodiments, the *Lactobacillus reuteri* comprises *Lactobacillus reuteri* strain DSM-20016. In some embodiments, the *Lactobacillus reuteri* comprises *Lactobacillus reuteri* strain 149.

In some embodiments, the level of one or both of *Megasphaera elsdenii* strains 14-14 and ATCC-25940 are measured in the contacted culture. In some embodiments, the level of one, two, three, four, five, six, or all seven of *Megamonas hypermegale* strains ART12/1, NCTC10570, DSM-1672T, ABXD-Z48, ABXD-N8, ABXD-L39, and ABXD-AC41 are measured in the contacted clture. In some embodiments, the level of *Megamonas rupellensis* strain FM1025 is measured in the contacted culture. In some embodiments, the level of one, two, or all three of *Lactobacillus reuteri* strains JCM-1112, DSM-20016, and I49 are measured. In some embodiments, each of the strains disclosed herein is measured.

In some preferred embodiments, the bacterial culture is a simulation of cat colon inoculated with a cat fecal sample. Colon simulators are known in the art and are not limited. See, e.g., Van de Wiele T., Van den Abbeele P., Ossieur W., Possemiers S., Marzorati M. (2015) The Simulator of the Human Intestinal Microbial Ecosystem (SHIME®). In: Verhoeckx K. et al. (eds) The Impact of Food Bioactives on Health. Springer, Cham; incorporated herein by reference in its entirety. In some embodiments, the bacterial culture is a bioreactor.

In some embodiments, the test agent is contacted with (i.e., incubated with) the culture for at least about 6 hours, 12 hours, 24 hours, 36 hours, 48 hours, 60 hours or more prior to determining the level of the one or more bacterial species in the contacted culture. In some embodiments, the test agent is contacted with (i.e., incubated with) the culture for about 24 hours prior to determining the level of the one or more bacterial species in the contacted culture. In some embodiments, the test agent is contacted with (i.e., incubated with) the culture for about 48 hours prior to determining the level of the one or more bacterial species in the contacted culture.

In some embodiments, the control is an identical bacterial culture (e.g., comprising a fecal inoculum from the same animal or an aliquot of the same fecal sample used to make the fecal inoculum) to the bacterial culture contacted with the agent, except that it is not contacted with the agent. Other suitable controls are known in the art and are not limited.

In some embodiments, the one or more test agents are contacted with a plurality of bacterial cultures, each inoculated with a fecal sample from a separate cat. In some embodiments, the fecal samples are from obese cats. In some embodiments, the fecal samples are from lean cats.

The agent is not limited and may be any agent suitable for oral administration to a cat. In some embodiments, the agent may comprise mucins. In some embodiments, the mucins may be obtained from a pig or a chicken. In some embodiments, the agent may be a prebiotic or a probiotic.

Also disclosed herein are methods of screening test agents to identify candidate agents for treating, reducing the likelihood, or preventing obesity in a dog, comprising providing a bacterial culture comprising one or more bacterial species selected from *Eubacterium tenue* and *Clostridium hiranonis*, contacting the culture with the one or more test agents, determining the level of the one or more bacterial species in the contacted culture, and identifying the one or more test agents as candidate agents if the contacted culture has a decreased level of the one or more bacterial species as compared to a control.

In some embodiments, the culture further comprises mucus (e.g., mucus beads). In some embodiments, the culture is or has been obtained with a dog fecal sample inoculum.

In some preferred embodiments, the bacterial culture is a simulation of dog colon inoculated with a dog fecal sample. Colon simulators are known in the art and are not limited. In some embodiments, the bacterial culture is a bioreactor.

In some embodiments, the test agent is contacted with (i.e., incubated with) the culture for at least about 6 hours, 12 hours, 24 hours, 36 hours, 48 hours, 60 hours or more prior to determining the level of the one or more bacterial species in the contacted culture. In some embodiments, the test agent is contacted with (i.e., incubated with) the culture for about 24 hours prior to determining the level of the one or more bacterial species in the contacted culture. In some embodiments, the test agent is contacted with (i.e., incubated with) the culture for about 48 hours prior to determining the level of the one or more bacterial species in the contacted culture.

In some embodiments, the control is an identical bacterial culture (e.g., comprising a fecal inoculum from the same animal or an aliquot of the same fecal sample used to make the fecal inoculum) to the bacterial culture contacted with the agent except that it is not contacted with the agent. Suitable controls are known in the art and are not limited.

In some embodiments, the one or more test agents are contacted with a plurality of bacterial cultures, each inoculated with a fecal sample from a separate dog. In some embodiments, the fecal samples are from obese dogs. In some embodiments, the fecal samples are from lean dogs.

The agent is not limited and may be any agent suitable for oral administration to a dog. In some embodiments, the agent may comprise mucins. In some embodiments, the mucins may be obtained from a pig or a chicken. In some embodiments, the agent may be a prebiotic or a probiotic.

EXAMPLES

Example 1

Obesity in domesticated animals is a growing problem. According to recent findings, more than 45% of dogs and 58% of cats can be classified as overweight or obese. Like in humans, it is known that the gut microbiome is altered in obese animals compared to lean animals, and that modulation of the gut microbiome may be an effective method for treating and preventing obesity. However, little research has been done to understand the microbiome composition of obese versus lean domesticated animals.

Methods

Using novel high resolution quantitative sequencing methods, the presence and abundance of 85 bacterial species commonly found in the gut of cats and dogs was analyzed. DNA from the feces of 8 lean and 8 obese cats, as well as 10 lean and 10 obese dogs, was sequenced. Sequencing was repeated three times. For bioinformatics analysis, blast was used as the alignment tool, comparing each of the query datasets to each of the sample libraries, and setting parameters for optimal, tight alignments favoring identity matching versus homology matching.

Results

All lean domesticated cats had a body condition score (BCS) of 5, and all obese domesticated cats had a BCS of 6.5 or higher (FIG. 1). Of 85 bacterial species analyzed, seven species presented clear differential expression in obsess vs. lean domesticated cats. Two species were greatly increased in obese animals, while five species were greatly decreased in obese animals. With high-resolution sequencing technology, specific strains within these seven bacterial species may also be identified.

Figure 2C:
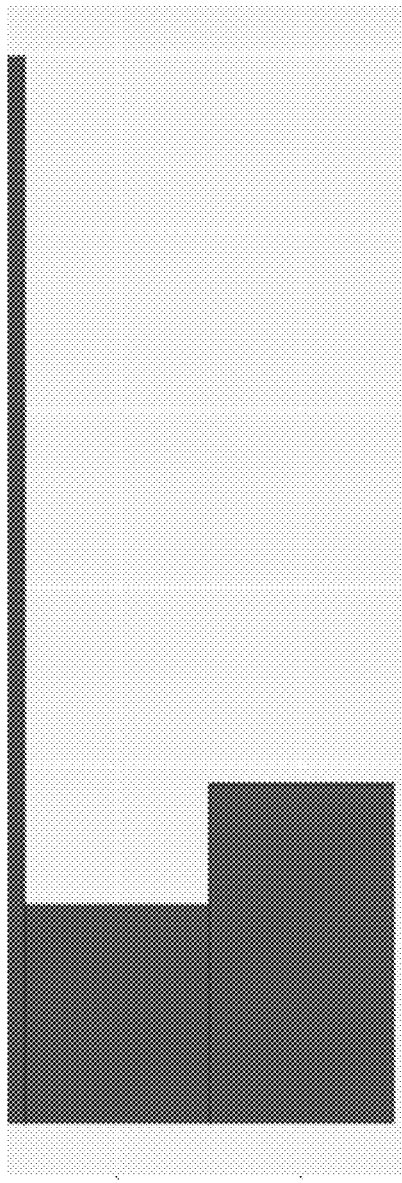
Figure 2D:
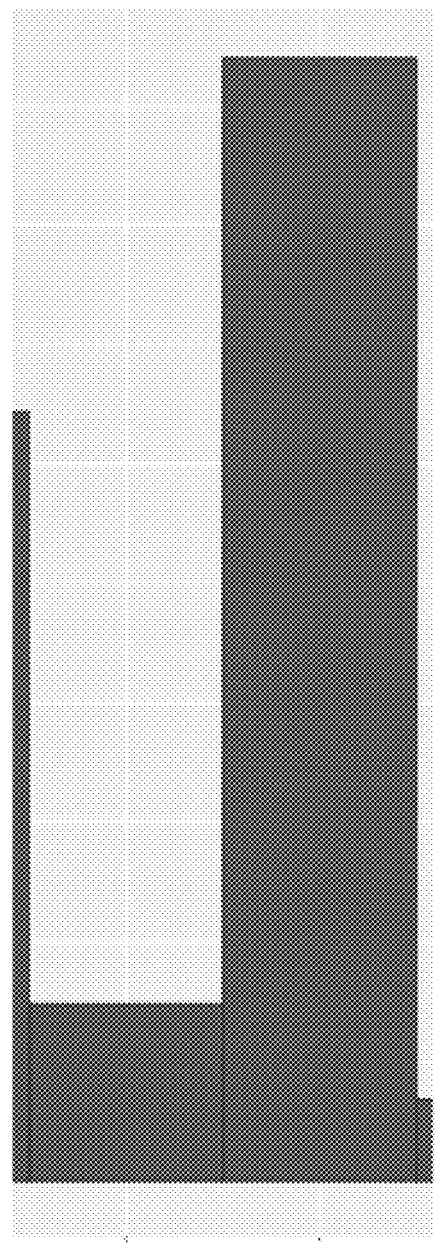

Two bacterial species were detected as potential markers of obesity: *Lactobacillus reuteri* and *Blautia schinkii*. *Lactobacillus reuteri* was highly expressed in 7 out of 8 obese cats (FIGS. 2A-2B). Interestingly, the highest *L. reuteri* levels were obtained from the cat with the highest BCS score (OC8, BCS of 9). The identification of *L. reuteri* as a potential marker of obesity in domesticated cats aligns with previously published observations in humans where qPCR data shows that *L. reuteri* is increased in obese humans compared to lean humans (Million M. et al., "Obesity-associated gut microbiota is enriched in *Lactobacillus reuteri* and depleted in *Bifidobacterium animalis* and *Methanobrevibacter smithii*" International Journal of Obesity, 36, 817-825 (2012)). Additional *Lactobacillus* species were examined at a lower stringency cut-off (e.g., *Lactobacillus salivarius*), but it was confirmed that *L. reuteri* is more expressed than *L. salivarius*, suggesting that not all *lactobacillus* species are increased in obese domesticated cats (FIGS. 2C-2D).

Figure 3A:
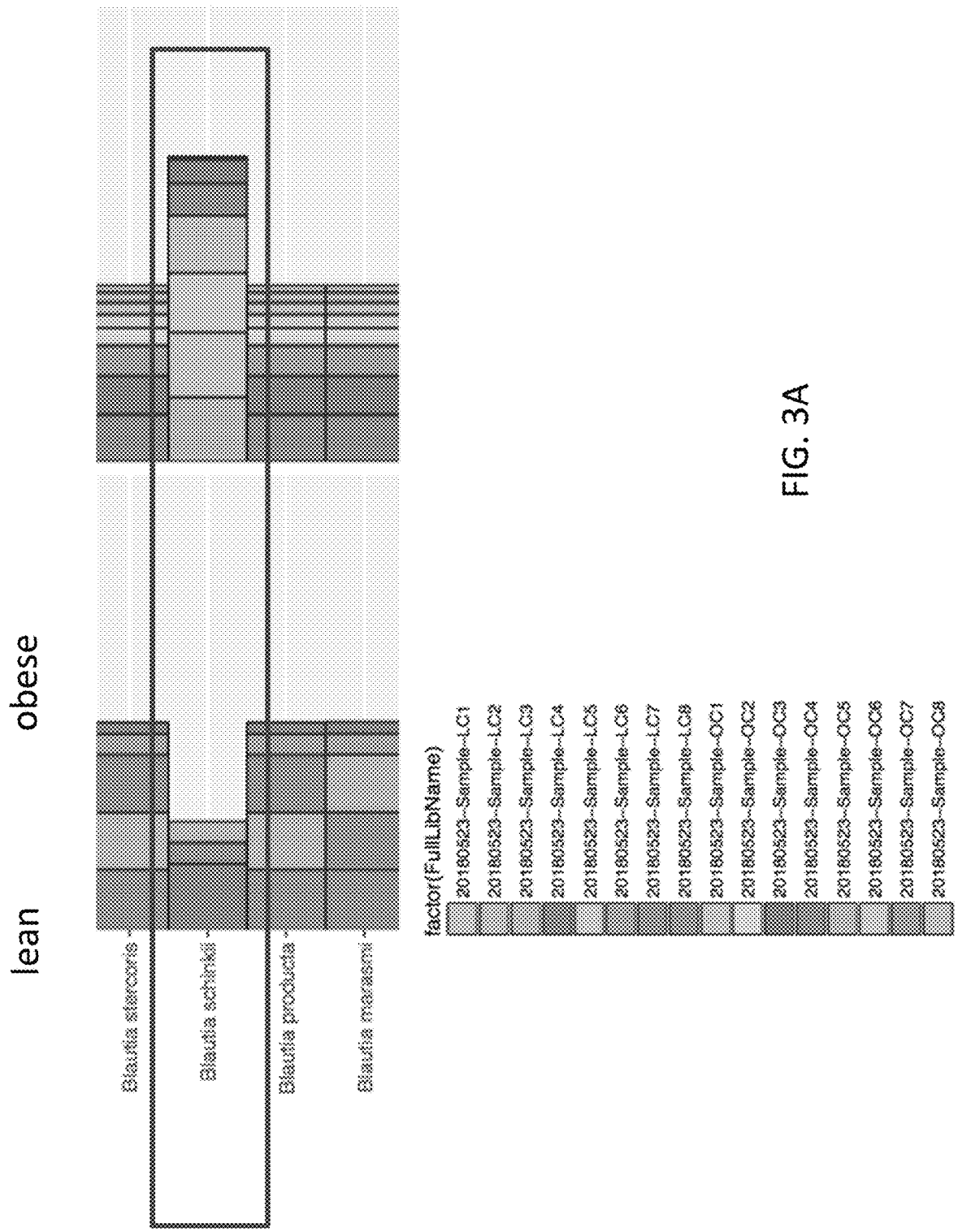
FIGS. 3A-3C demonstrate *Blautia schinkii* as a possible marker of obesity in domesticated cats.
Figure 3B:
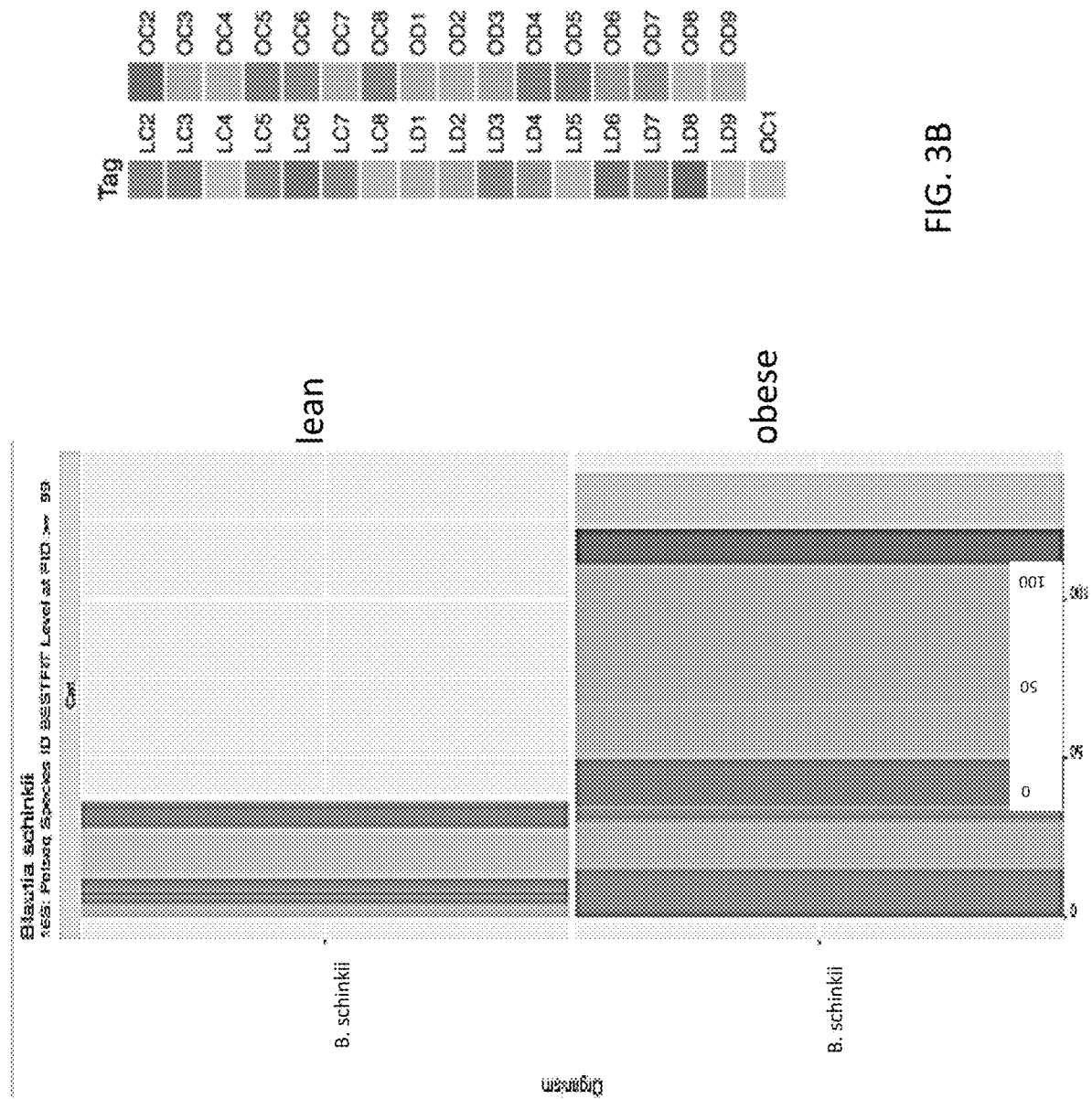
Figure 3C:
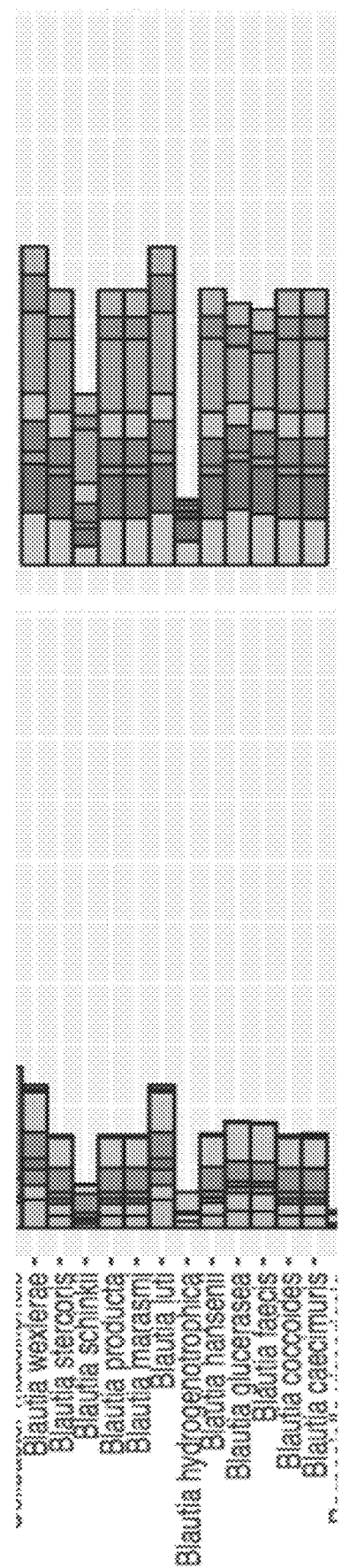

Multiple *Blautia* species were detected during the initial bacterial screen. *Blautia schinkii* exhibited high expression levels in all obese cats, and only exhibited minor expression in a few lean cats (FIGS. 3A-3B), and thus may act as a marker for obesity. Upon completion of the first experiment, expression levels for the other *Blautia* species did not vary significantly between obese and lean domesticated cats. However, after repeating the experiment, a clear difference was seen in all *Blautia* species (12 species) between obese cats and lean cats (FIG. 3C). Thus, additional *Blautia* species may also act as biomarkers for obesity in domesticated cats. Previous NGS analysis in humans shows that *Blautia* species are increased in obese humans. However, the study did not provide any specific data on *B. schinkii* (Kassai C, et al. "Comparison of the gut microbiota composition between obese and non-obese individuals in a Japanese population, as analyzed by terminal restriction fragment length polymorphism and next-generation sequencing" *BMC Gastroenterology* 15:100 (2015)). In addition, a recent paper shows that obese cats have a decrease in *Blautia* species (Pallotto, M. R., et al., "Effects of weight loss with a moderate-protein, high-fiber diet on body composition, voluntary physical activity, and fecal microbiota of obese cats" *Am. J. Vet. Res.* 79:181-190 (2018)). However, the data obtained in this study suggests that different *Blautia* species behave differently.

Figure 4A:
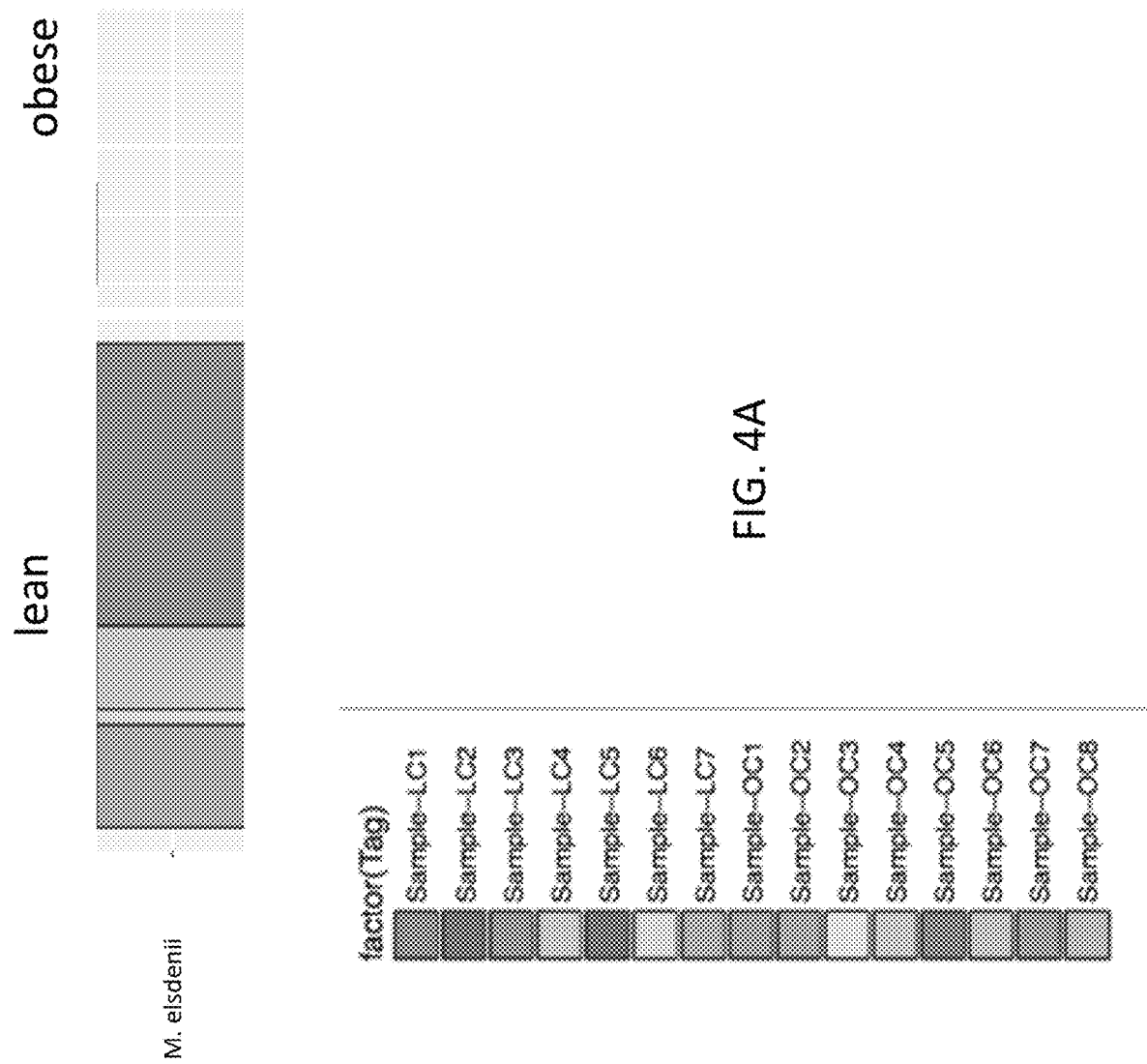
FIGS. 4A-4C demonstrate *Megasphaera elsdenii* as a possible marker of leanness in domesticated cats.
Figure 4B:
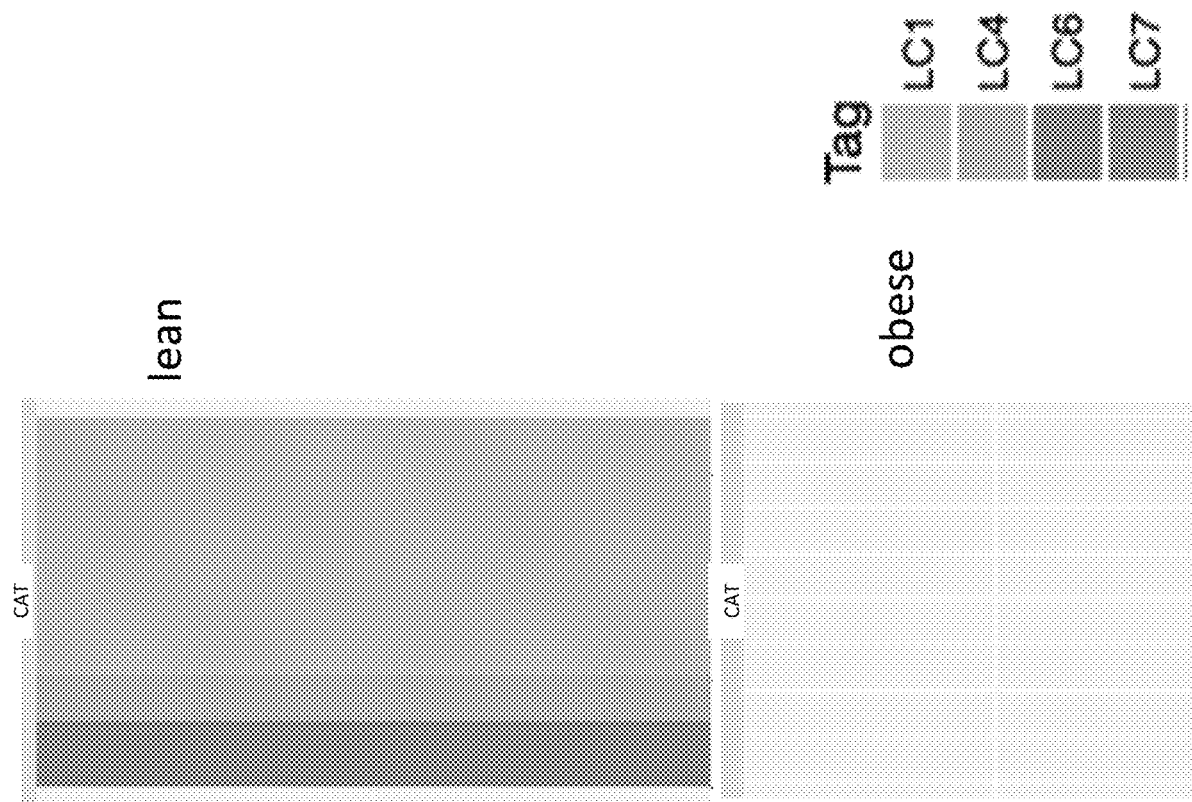
Figure 4C:
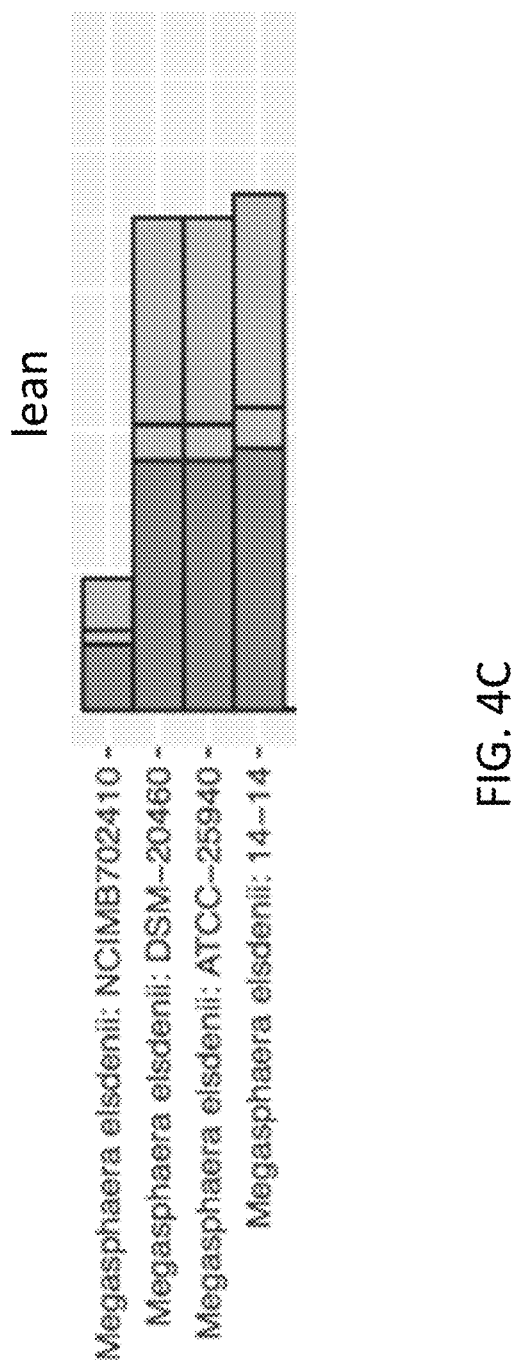
Figure 5A:
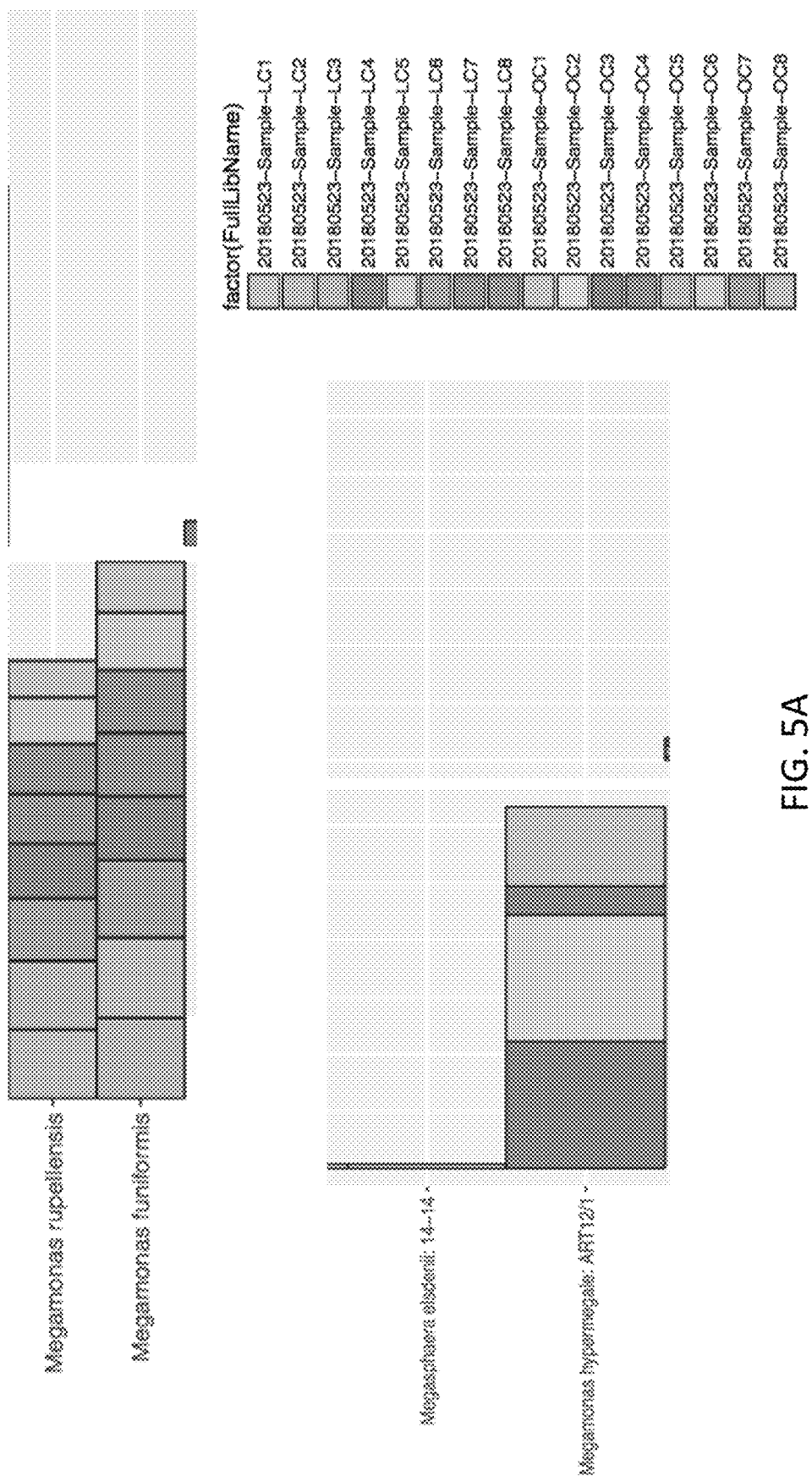
FIGS. 5A-5B demonstrate *Megamonas rupellensis, Megamonas funiformis*, and *Megamonas hypermegale* as possible markers of leanness in domesticated cats.
Figure 5B:
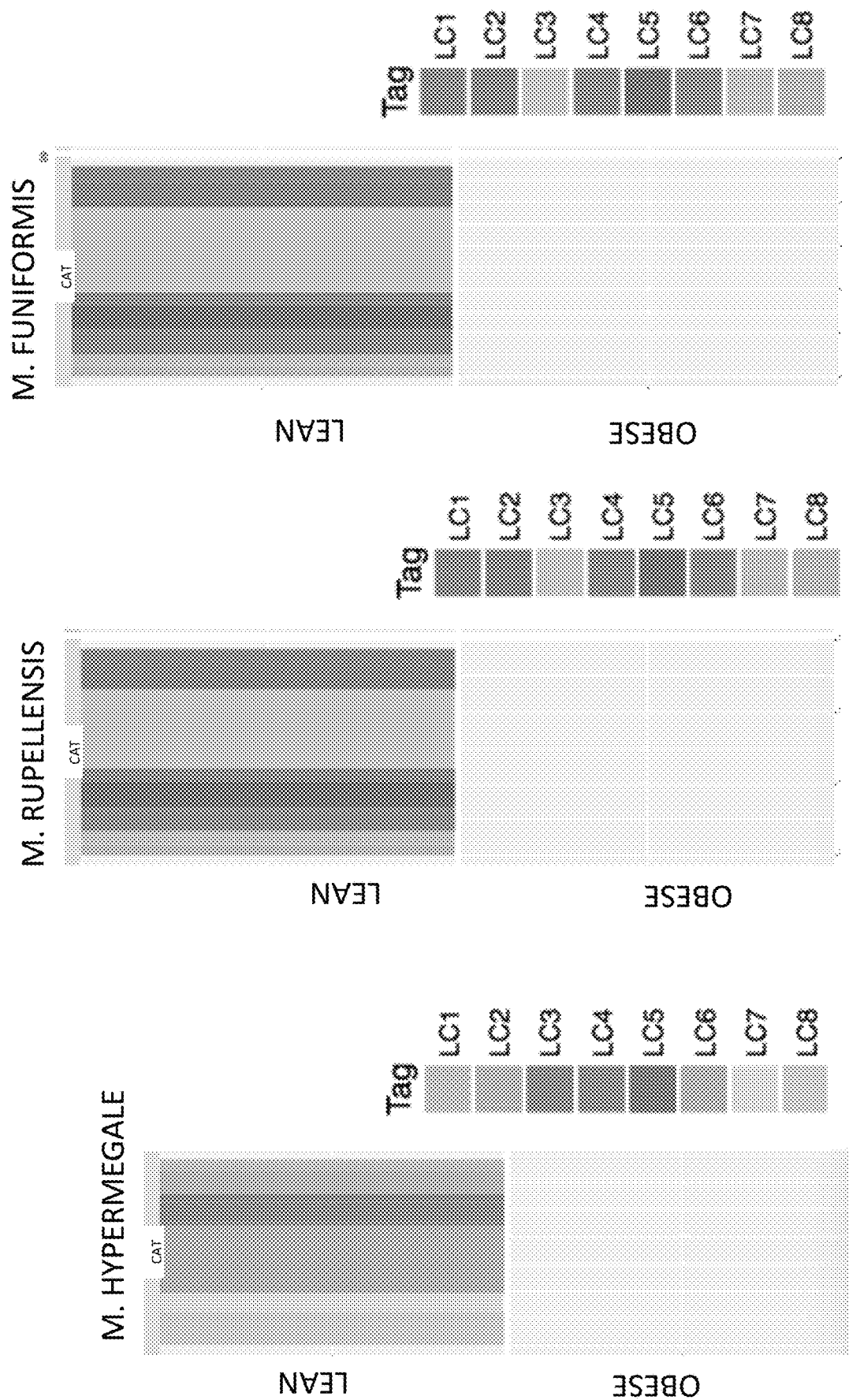

Additionally, five bacterial species were detected as markers of leanness: *Megasphaera elsdenii*, *Megamonas rupellensis*, *Megamonas funiformis*, *Megamonas hypermegale*, and *Bacteroides coprophilus*. *Megasphaera elsdenii*, *Megamonas rupellensis*, *Megamonas funiformis*, and *Megamonas hypermegale* were all highly expressed in lean cats and not detected in obese cats (FIGS. 4A-4B; FIGS. 5A-5B). Preliminary strain level analysis shows that not all strains of *M. elsdenii* are equally expressed. Strain 14-14 appears to have the highest expression and could be used as a marker of leanness (FIG. 4C). Preliminary strain level analysis for *M. hypermegale* indicates that it is the ART12/1 strain.

Figure 6A:
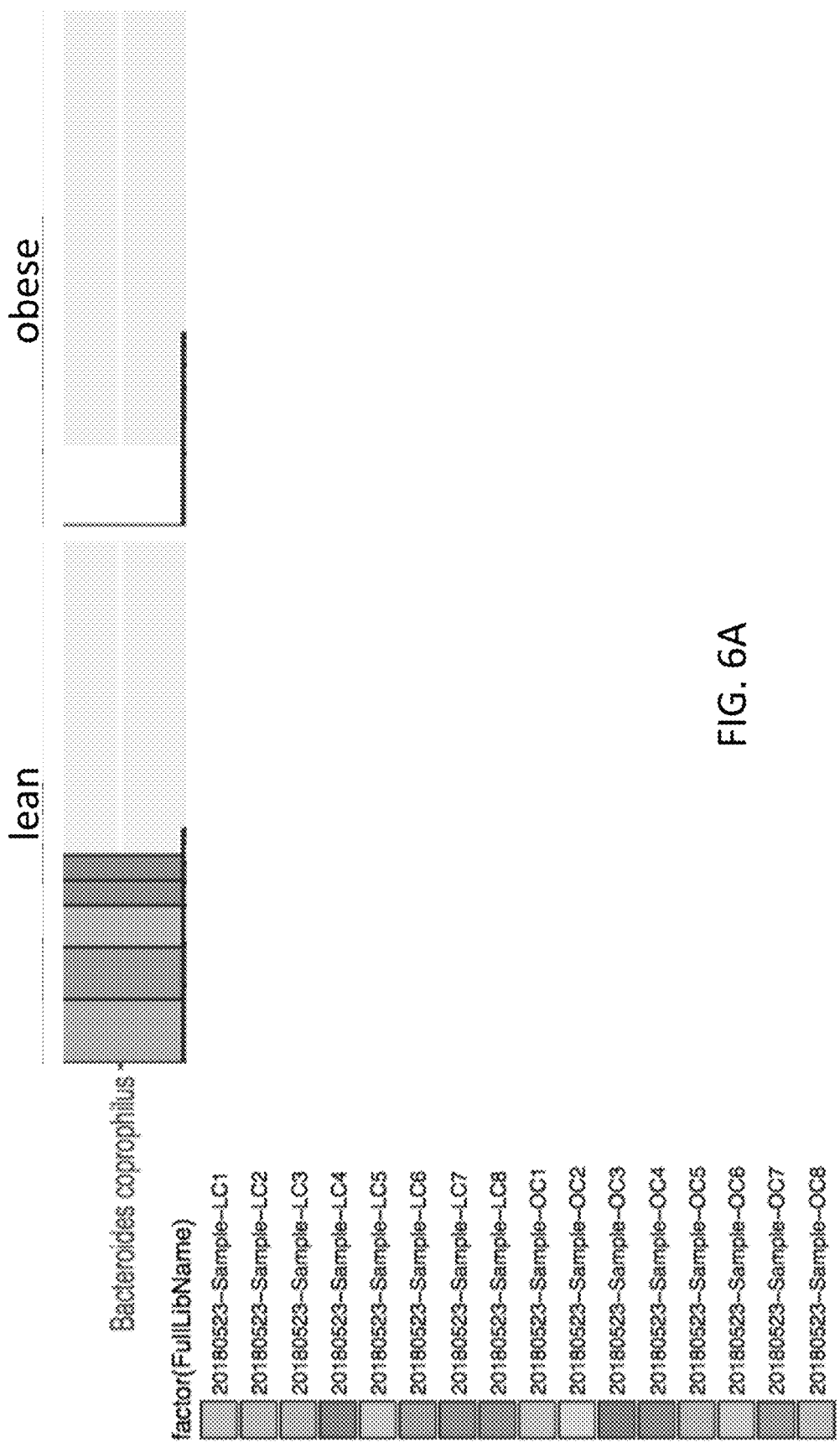
FIGS. 6A-6B demonstrate *Bacteroides coprophilus* as a possible marker of leanness in domesticated cats.
Figure 6B:
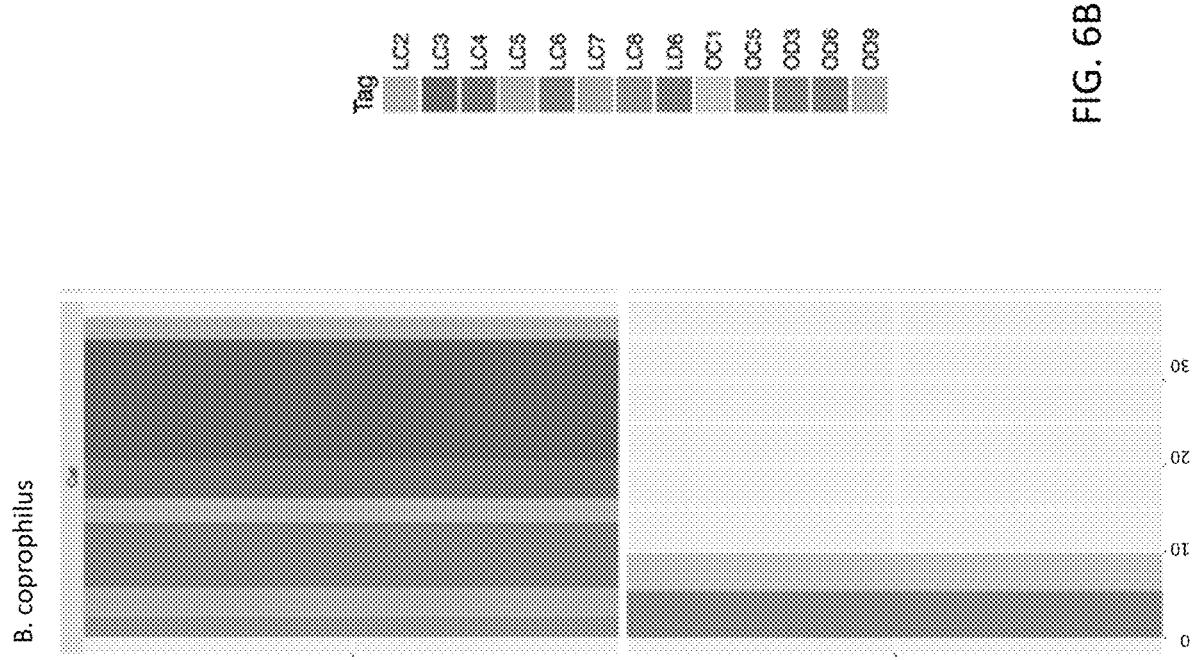

*Bacteroides coprophilus*, although slightly expressed in obese domesticated cats, was significantly more expressed in lean animals (FIG. 6A-6B). In the first experiment (FIG. 6A) no expression of *B. coprophilus* was seen in obese cats, while in the second experiment (FIG. 6B) some expression of *B. coprophilus* was seen in obese cats. Nonetheless, overall there is clearly higher expression of *B. Coprophilus* in lean cats than in obese cats, and *B. coprophilus* may act as a marker for leanness.

Figure 7A:
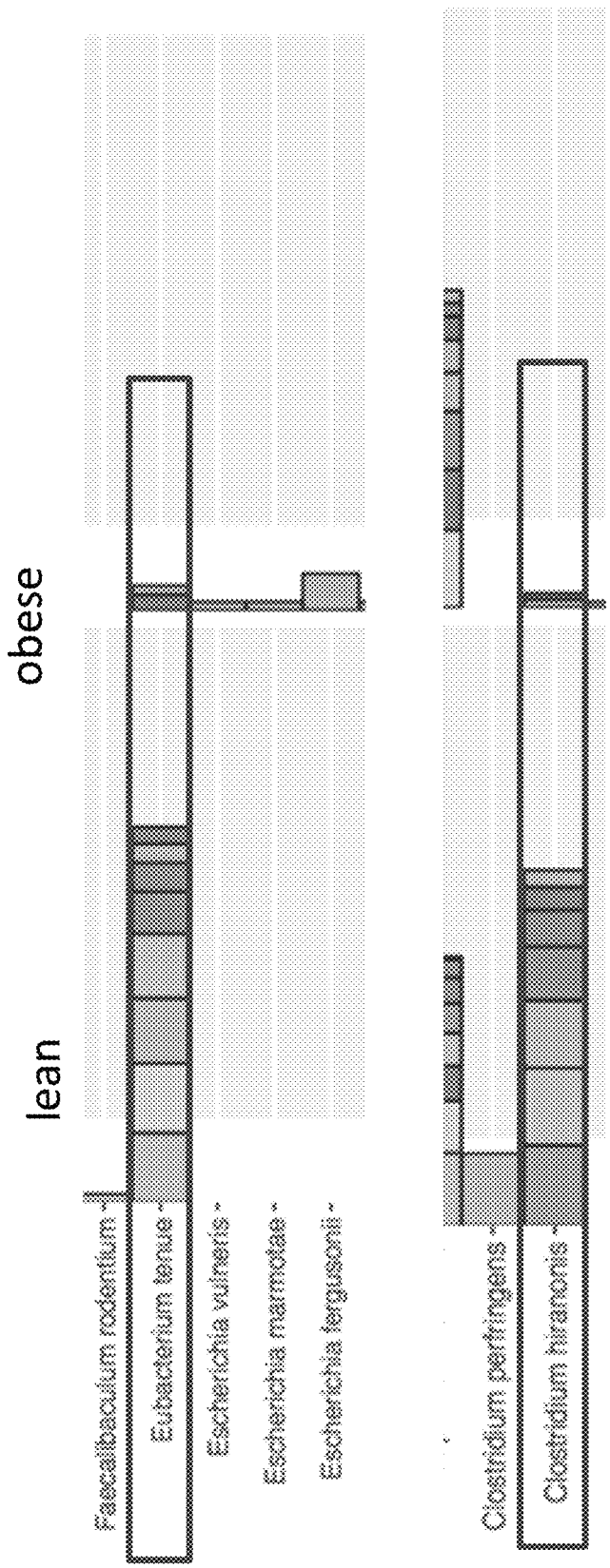
FIGS. 7A-7B demonstrate Eubacteroium *tenue* and *Clostridium hiranonis* as possible markers of leanness in domesticated dogs.
Figure 7B:
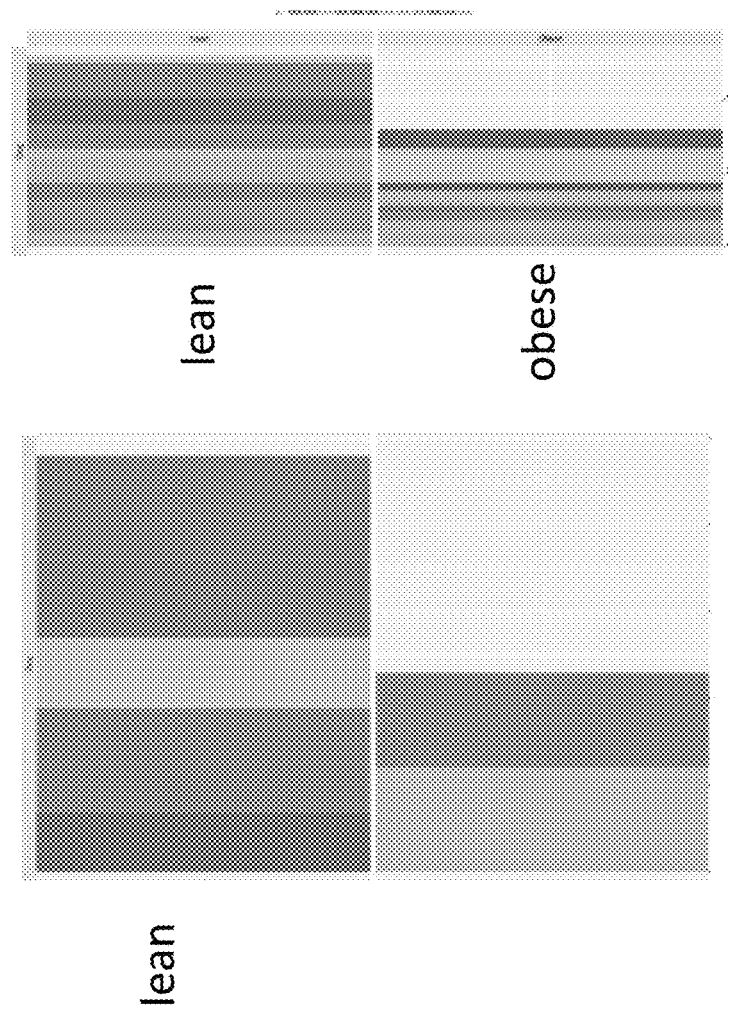
Figure 8A:
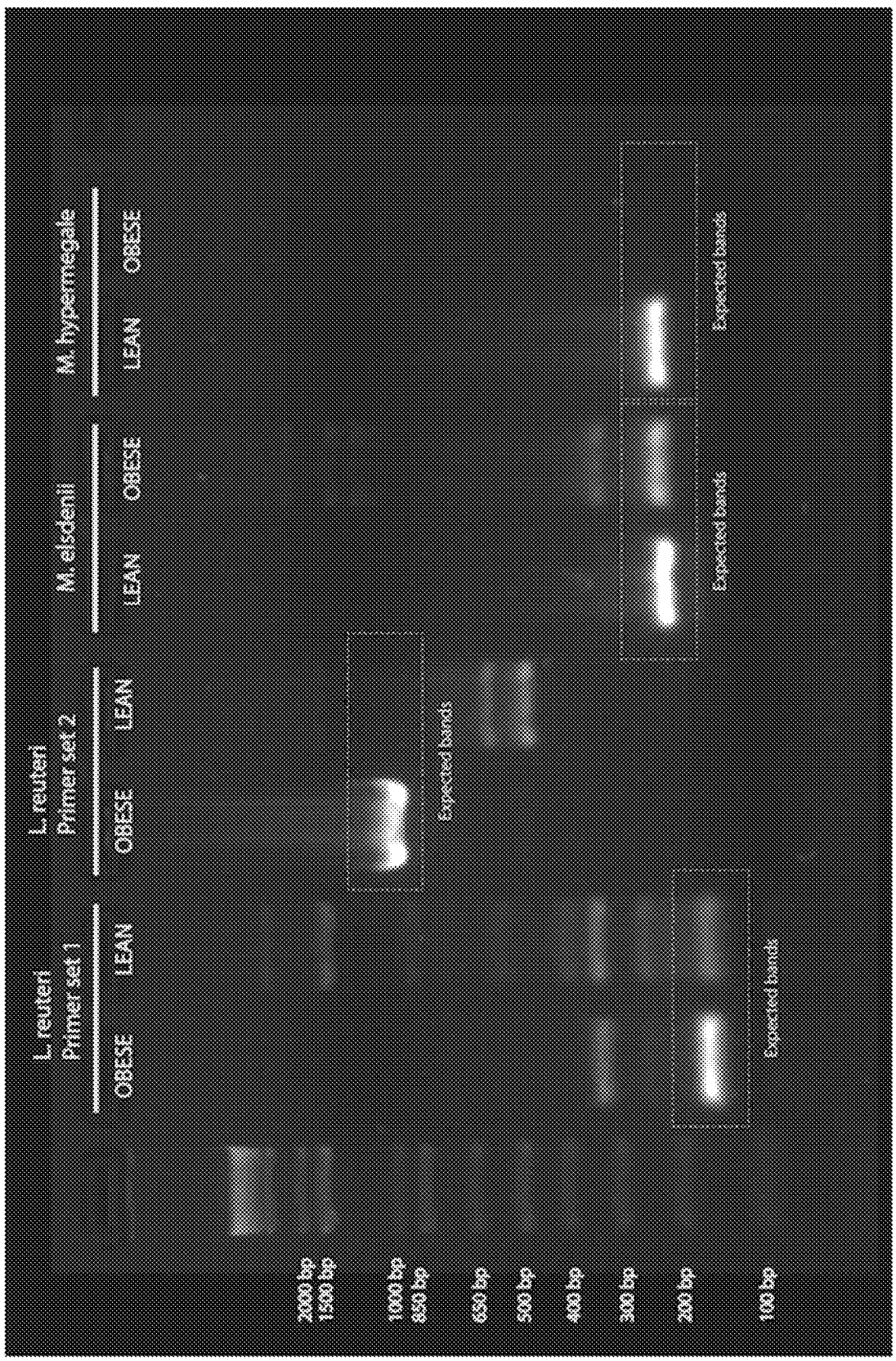
FIGS. 8A-8D demonstrate PCR validation of screening results.
Figure 8B:
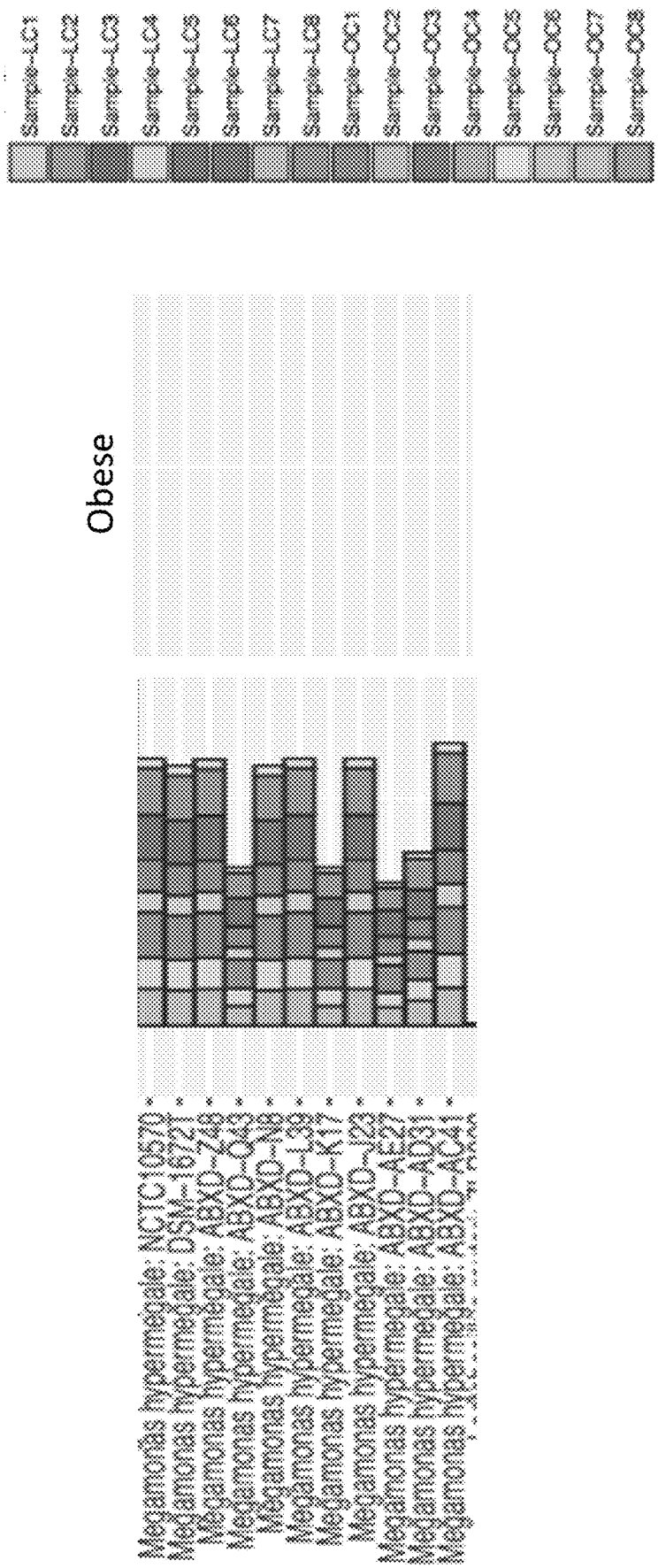
Figure 8C:
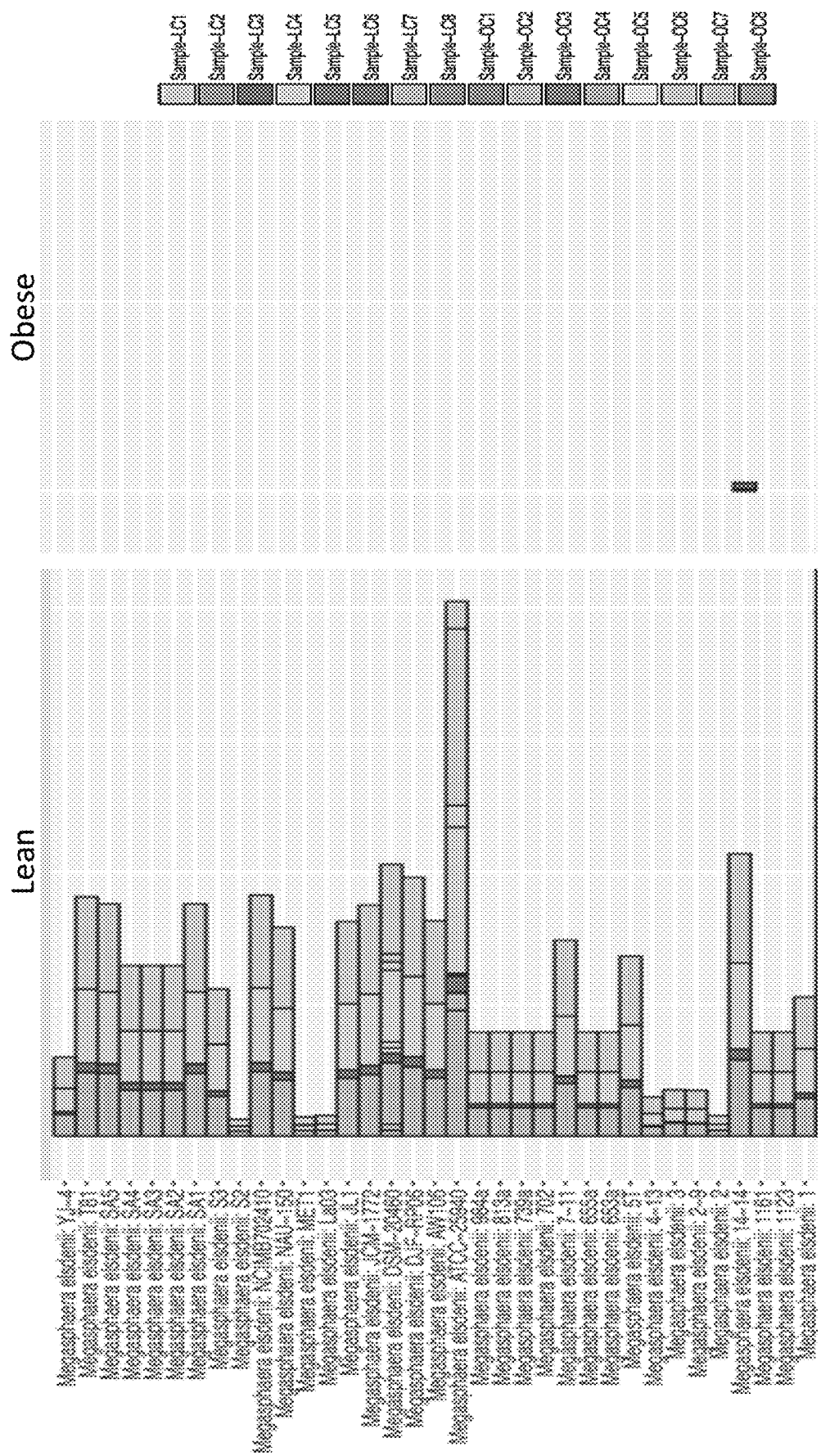
Figure 8D:
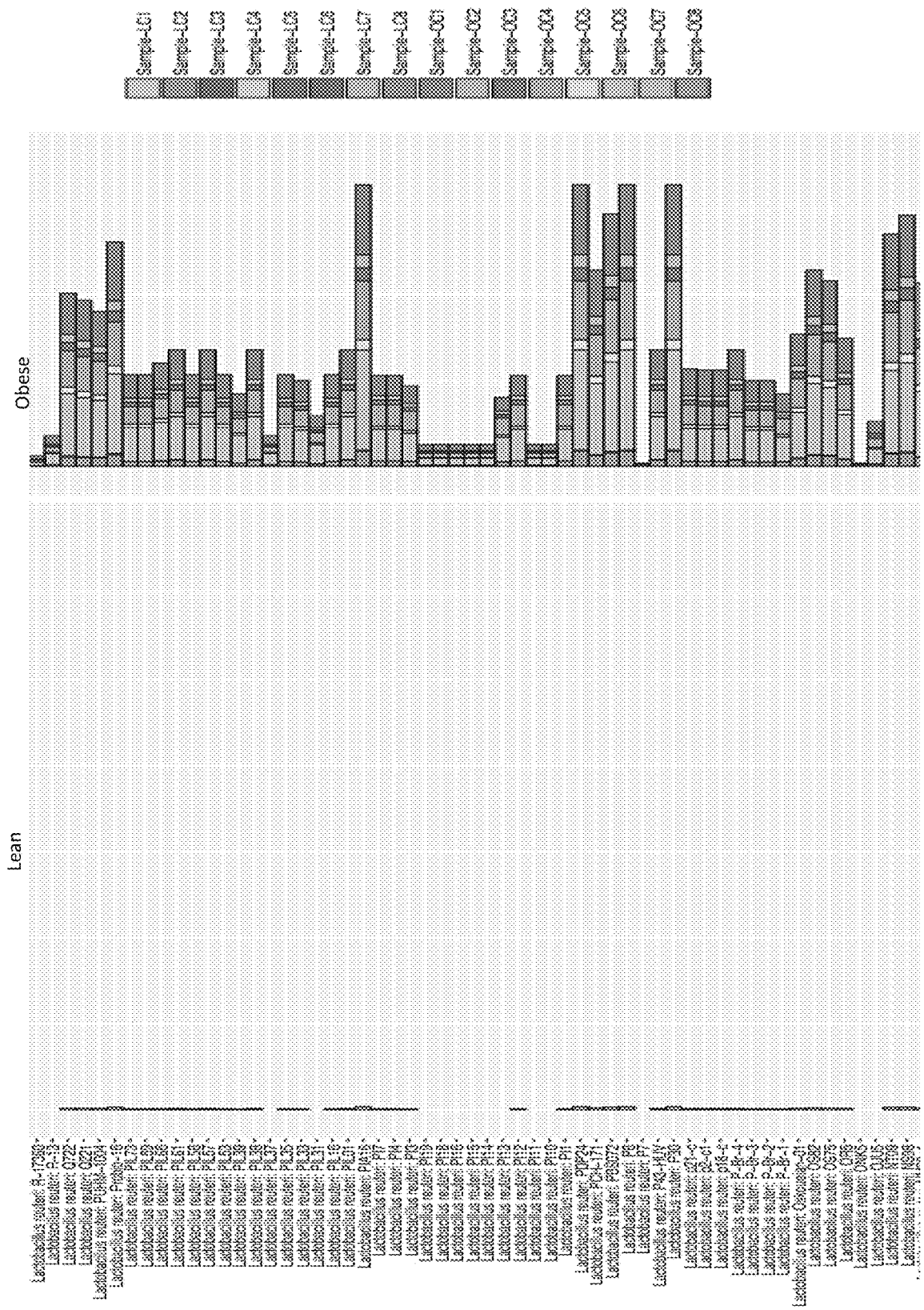
Figure 9A:
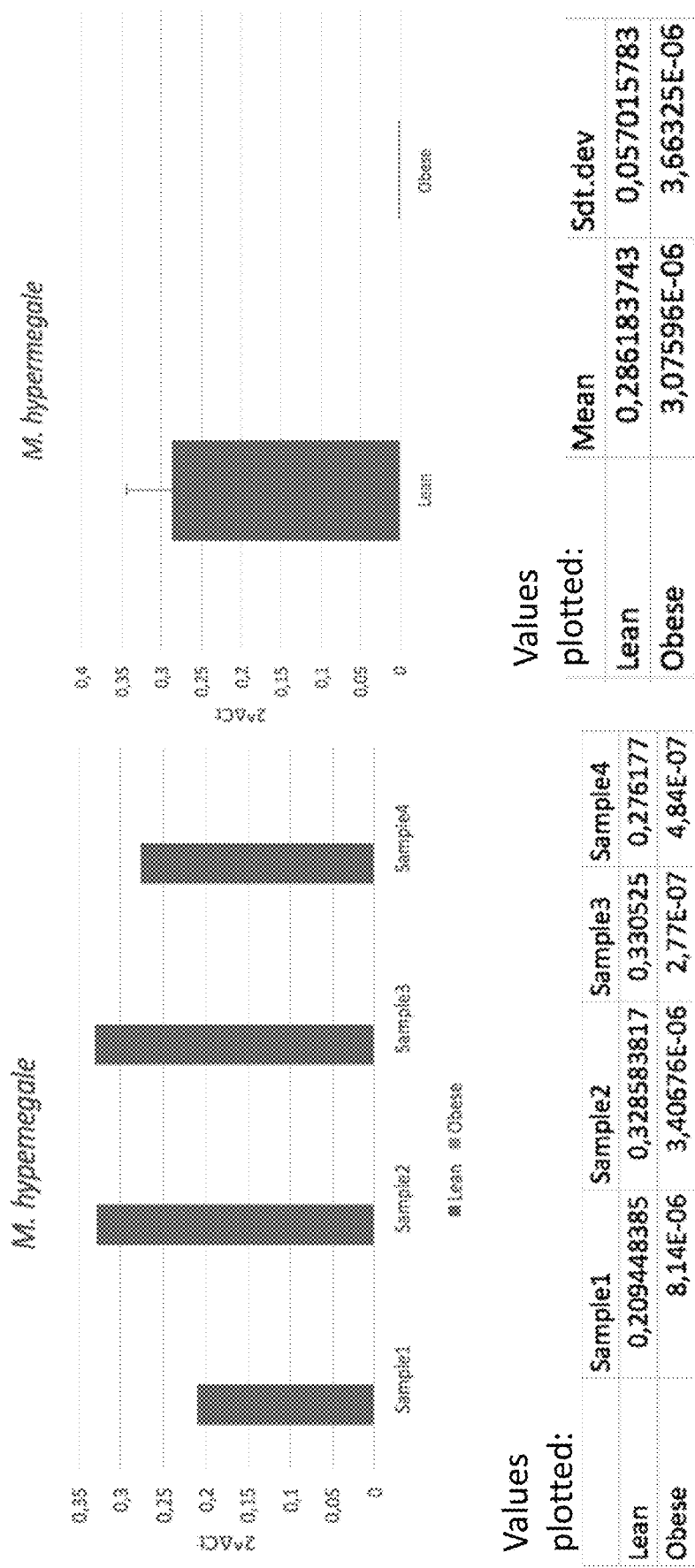
FIGS. 9A-9B demonstrate qPCR validation of screening results. Results were plotted in two different ways: some values were so low that they did not appear on the graph and so tables were provided which identified the numerical value being plotted.
Figure 9B:
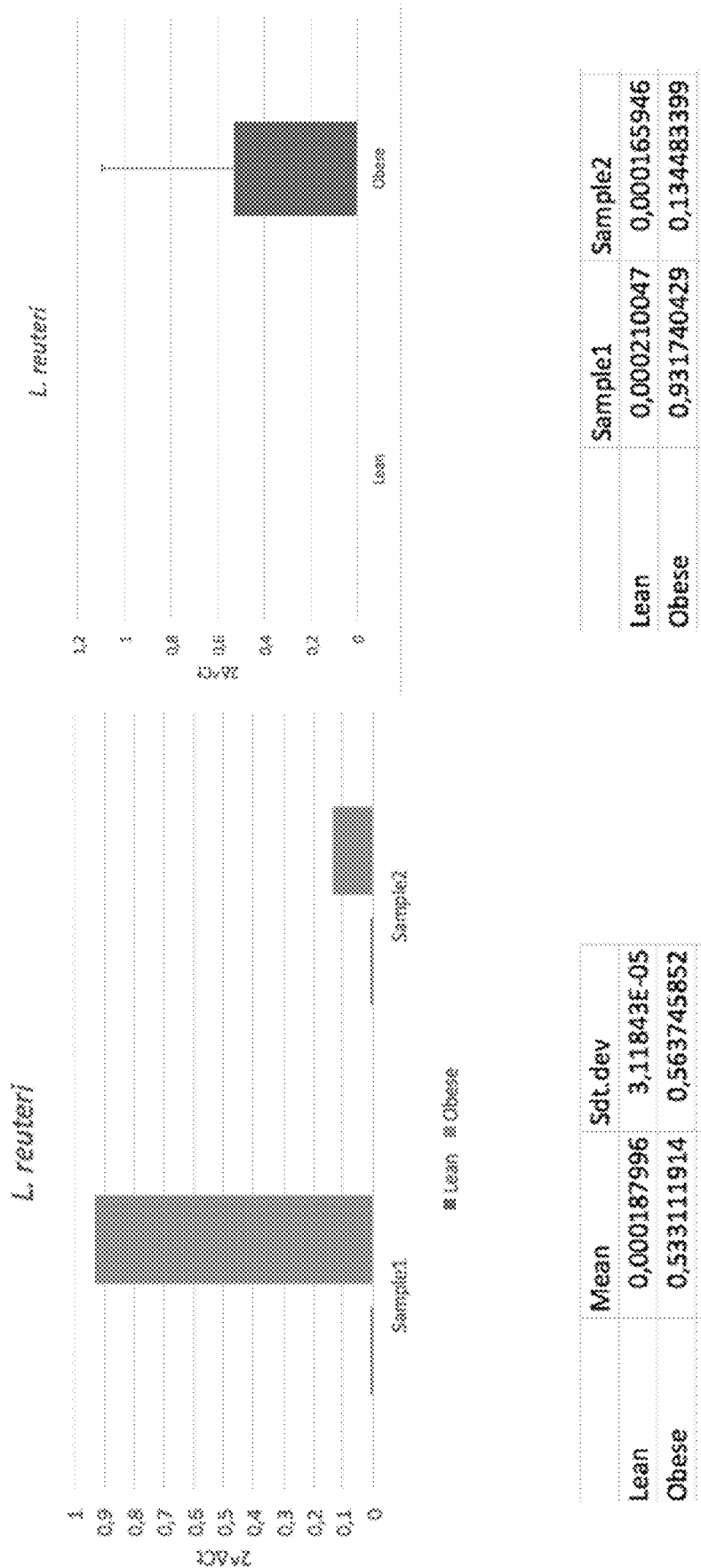
Figure 10B:
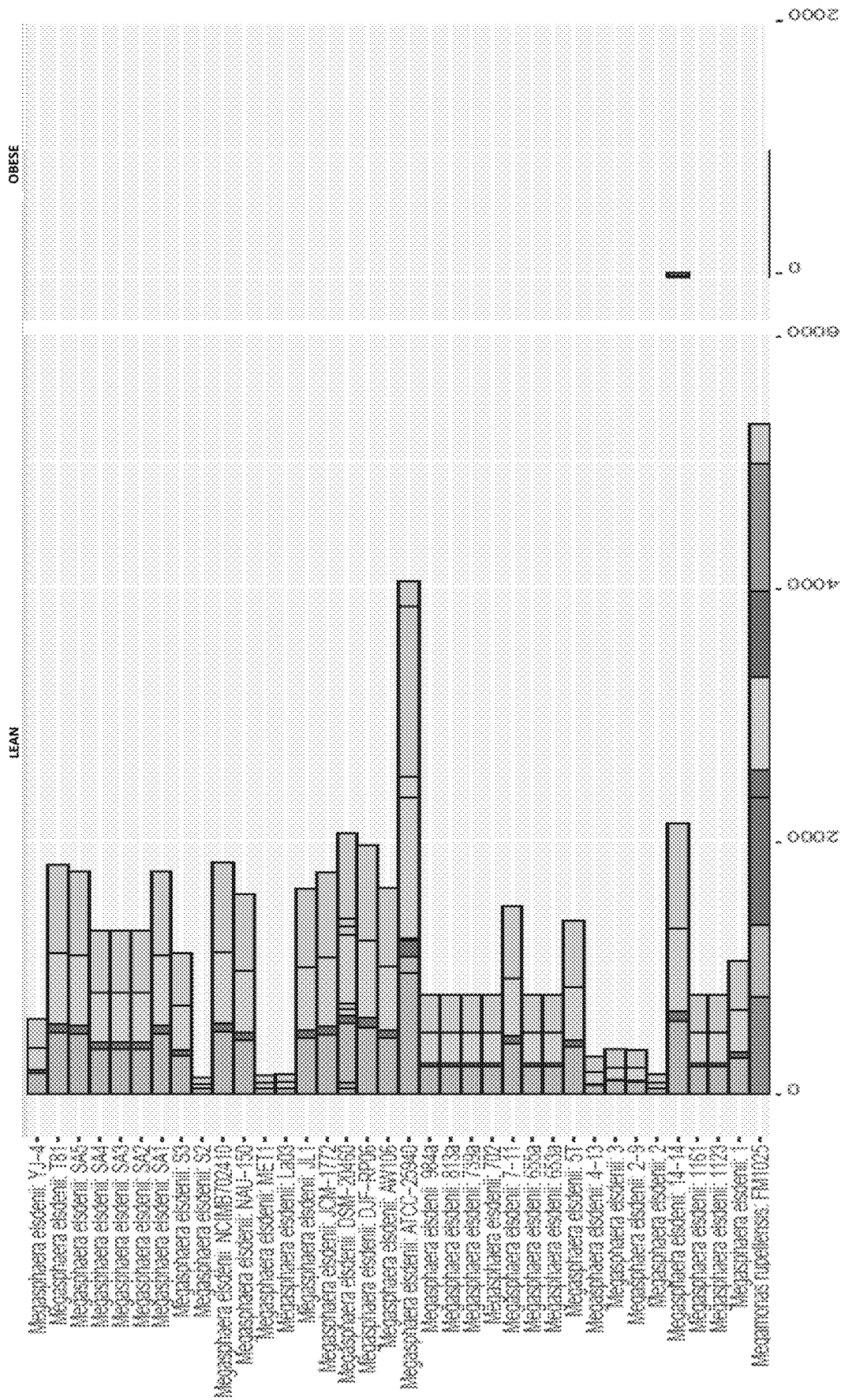
Figure 10B:
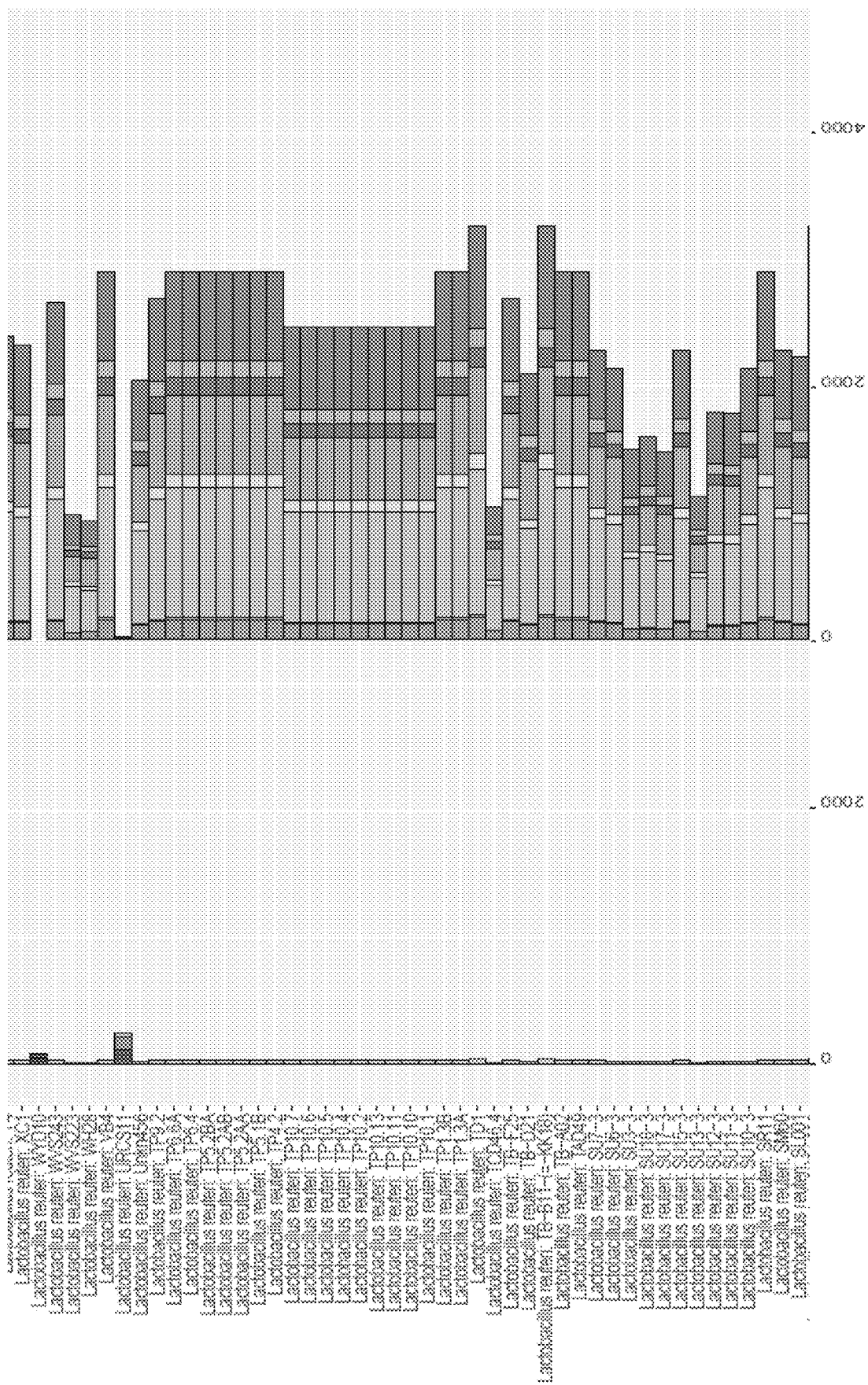
Figure 10B:
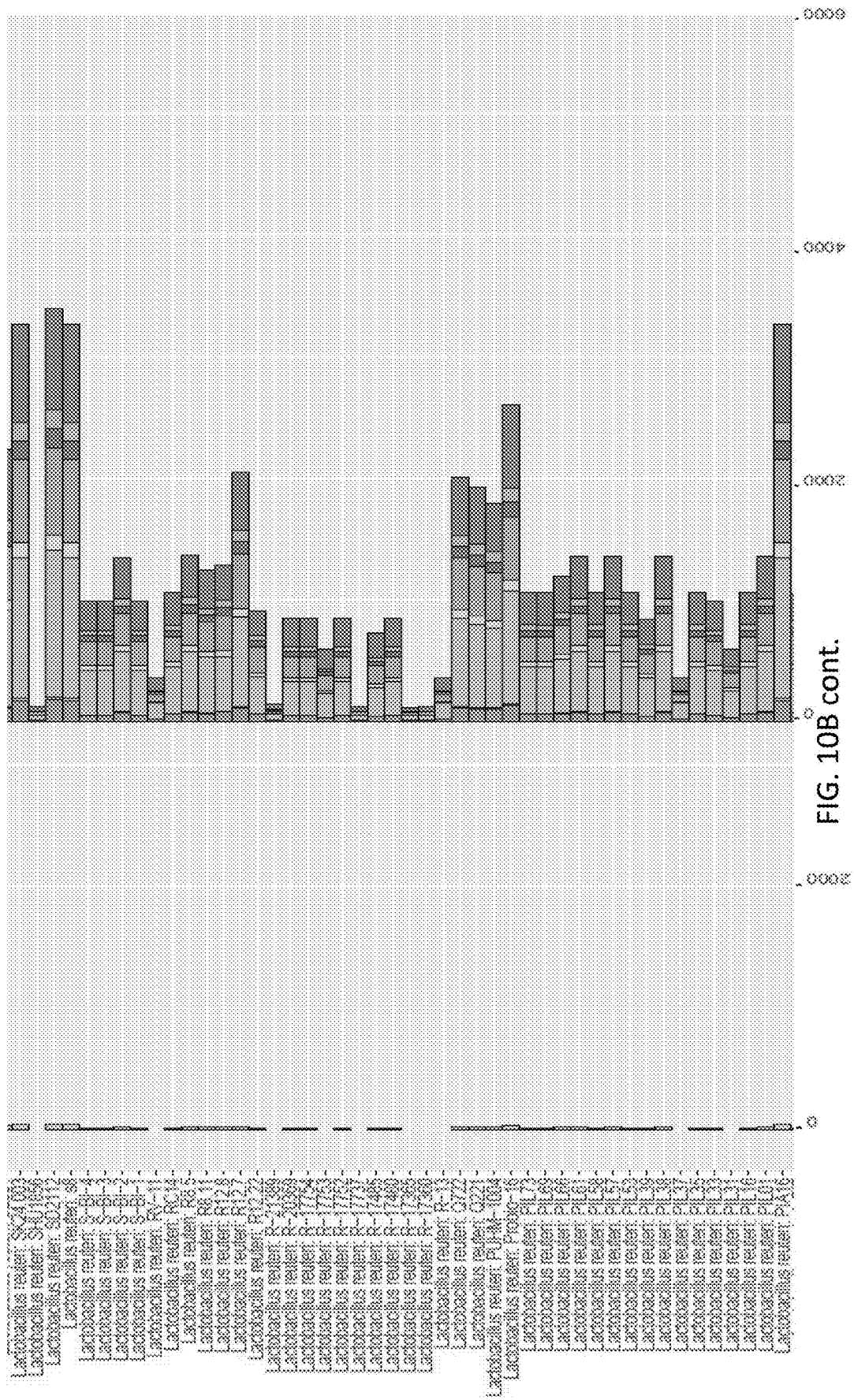
Figure 10B:
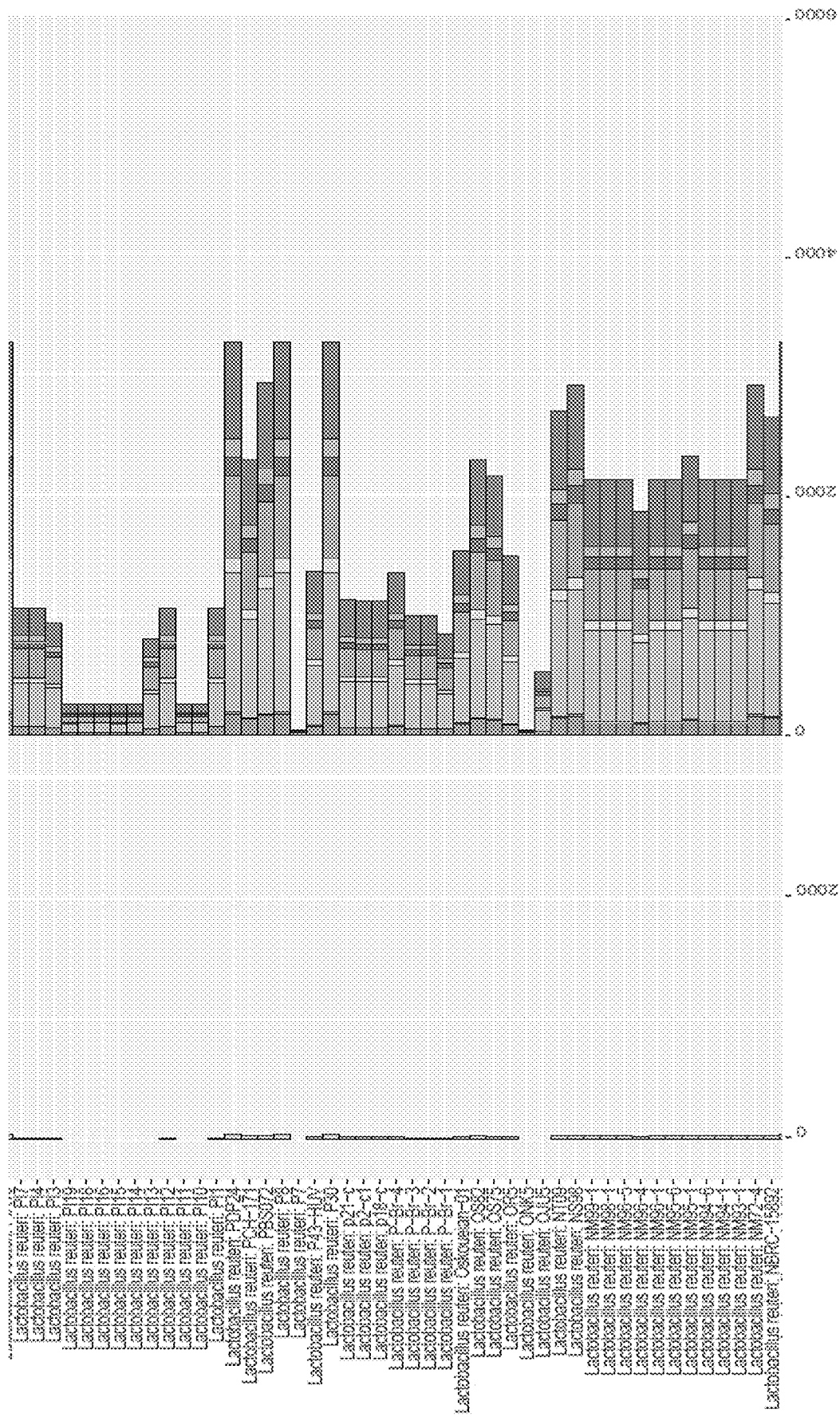
Figure 10B:
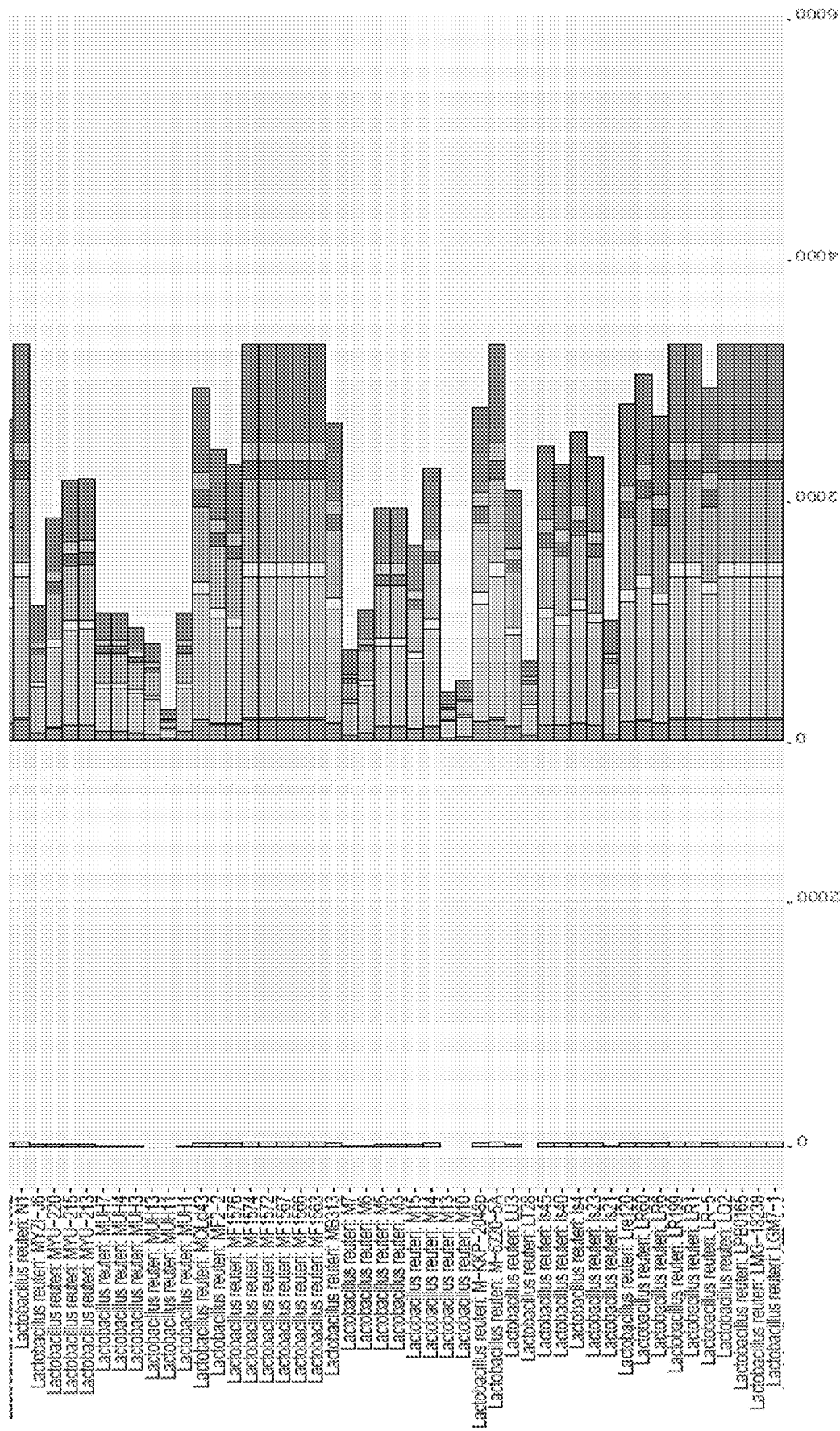
Figure 10B:
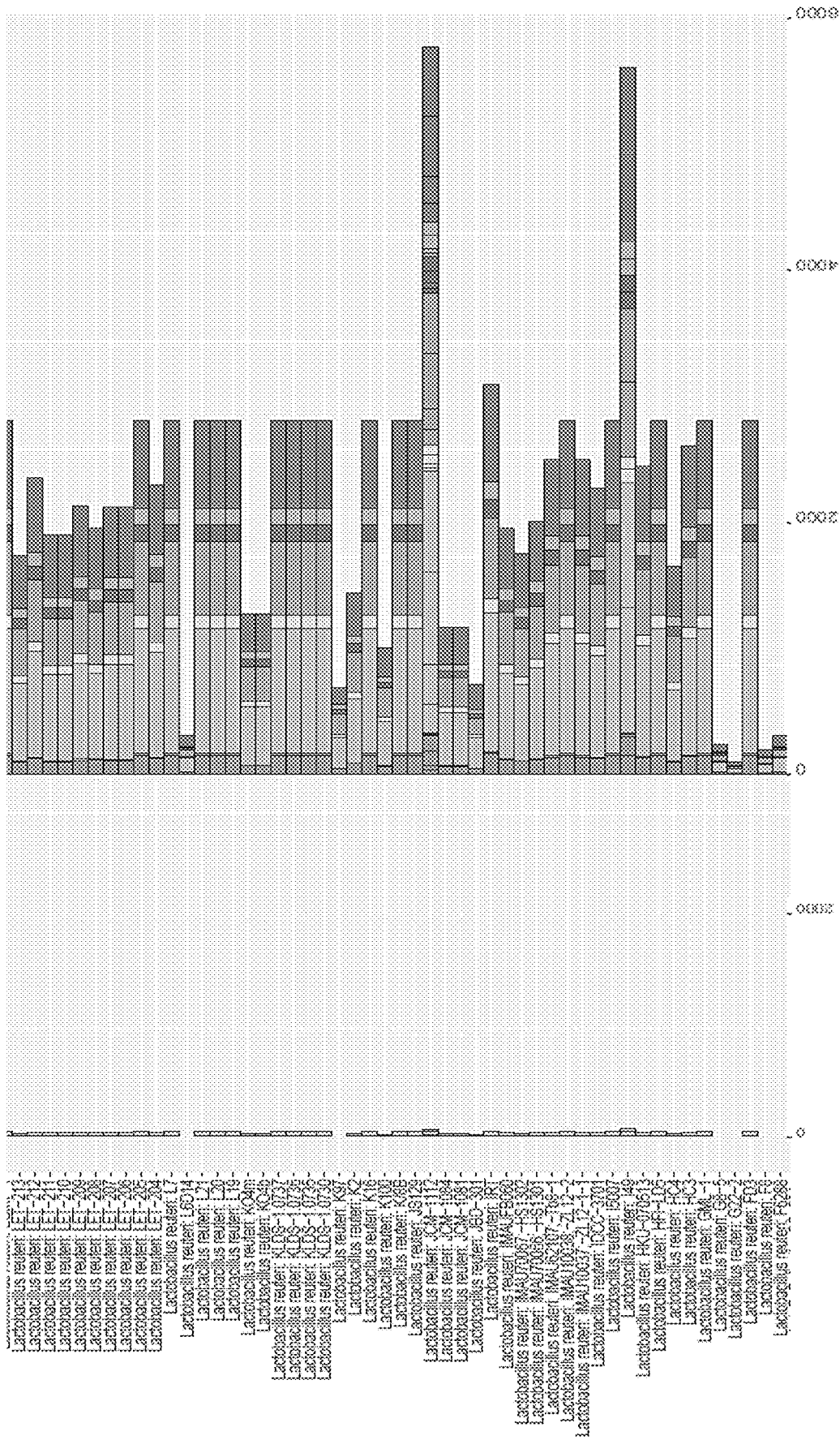
Figure 10B:
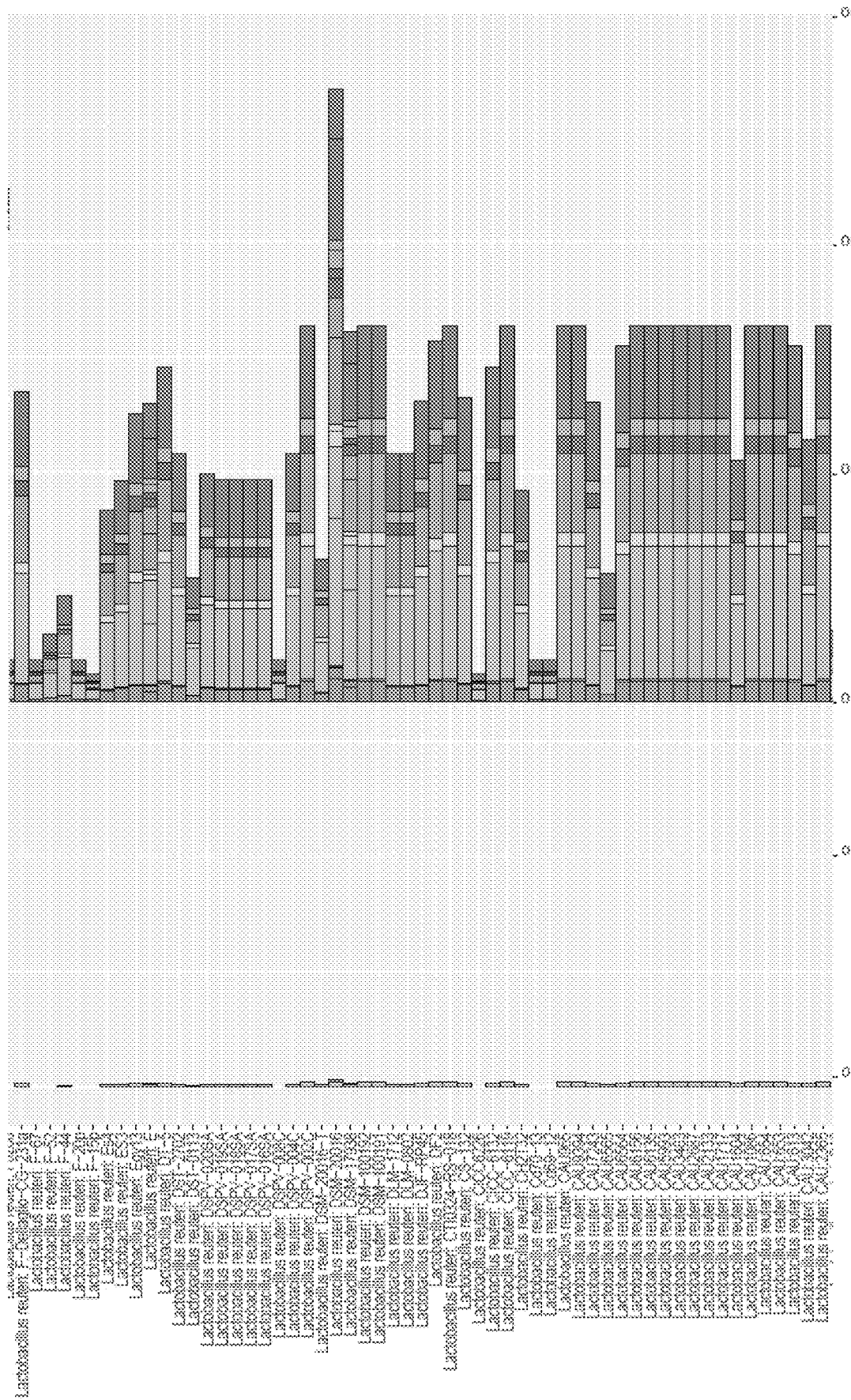
Figure 10B:
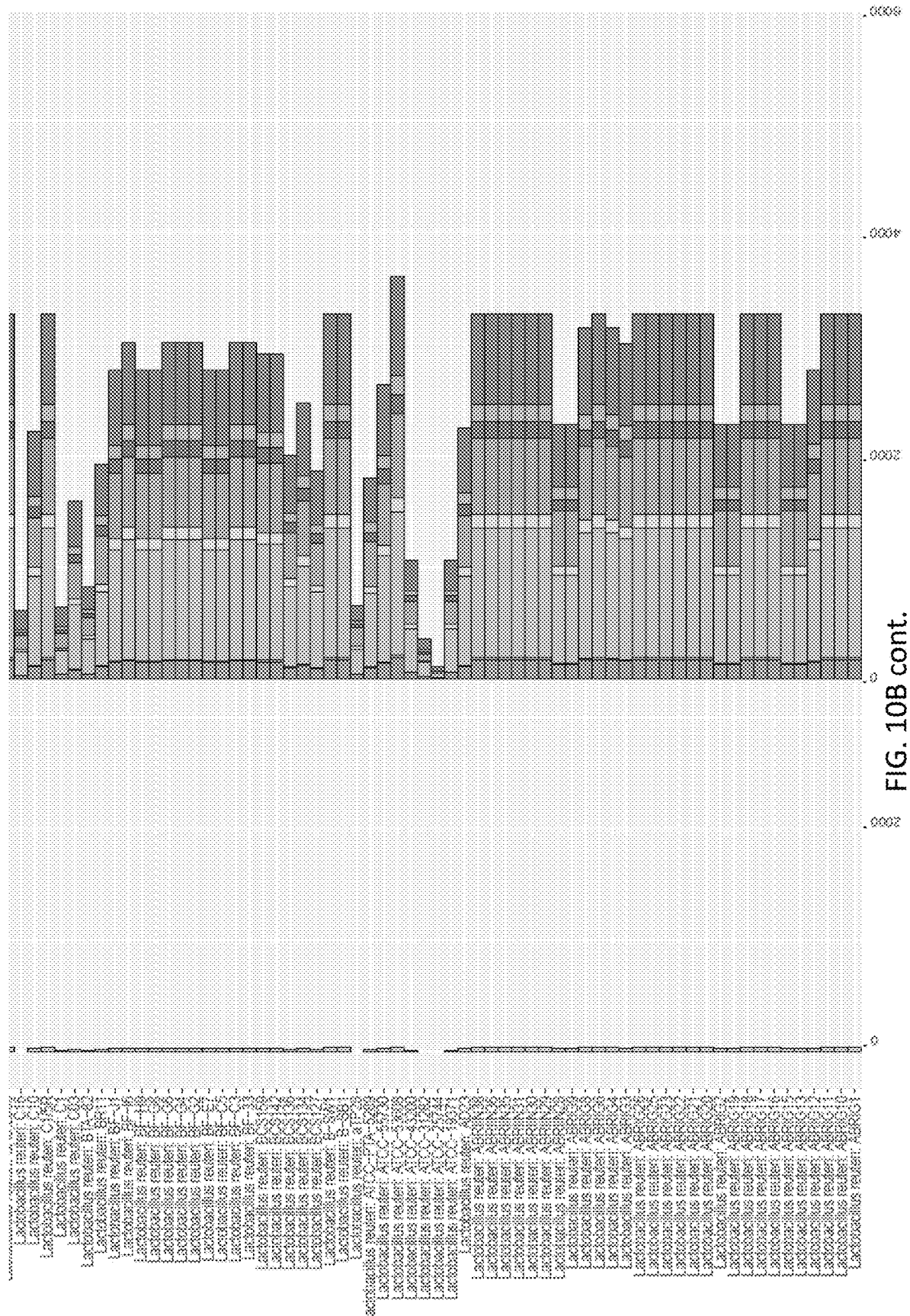
Figure 10B:
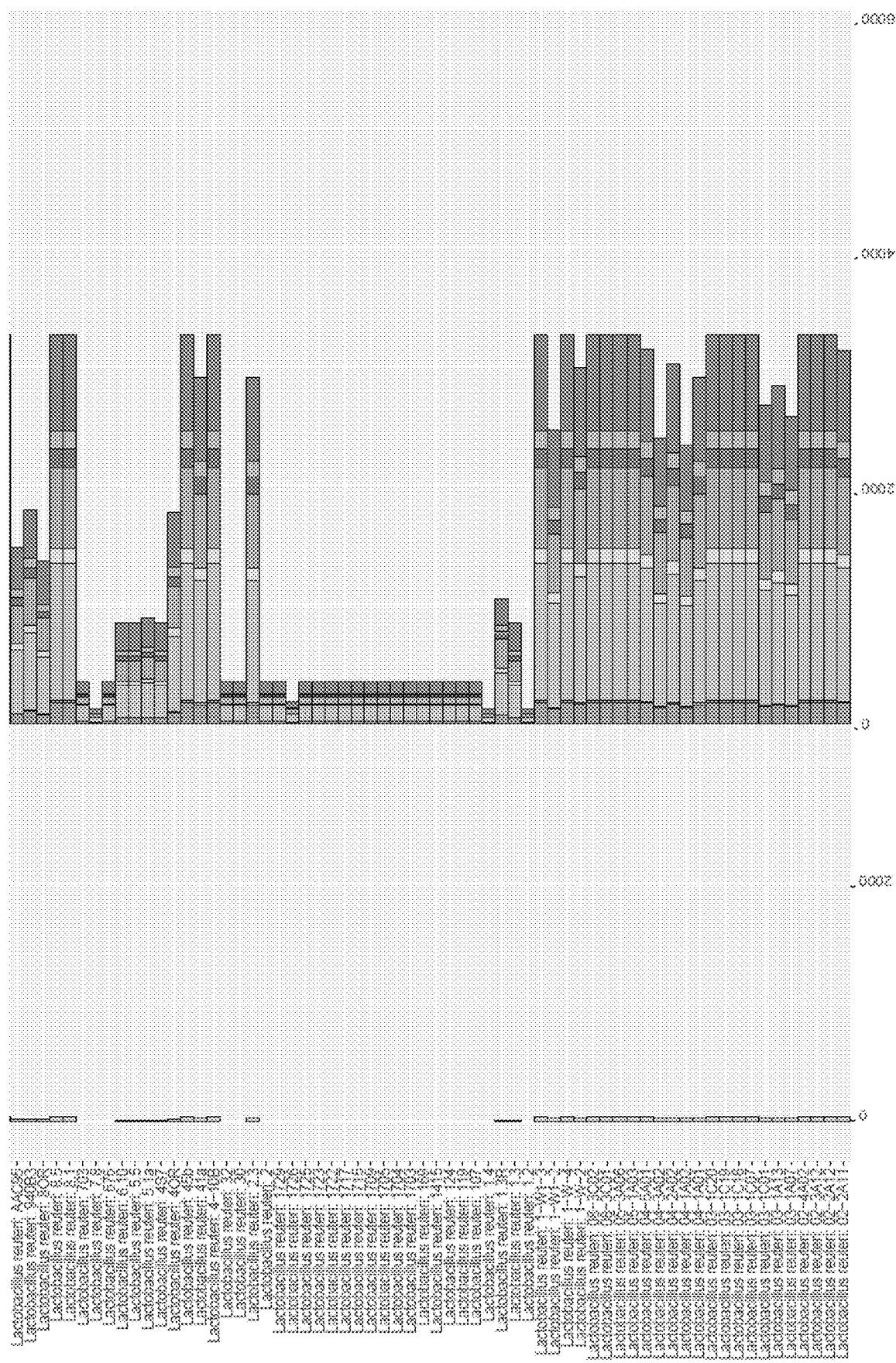

In addition to screening obese and lean cats for bacterial biomarkers for obesity, obese and lean dogs were also screened. Eubacteroium *tenue* and *Clostridium hiranonis* were both identified as possible markers of leanness. Although some expression of both *E. tenue* and *C. hiranonis* was found in obese dogs during the second run of the experiment (FIG. 7B), expression levels of both bacterial species were clearly higher in lean dogs. Thus, *E. tenue* and *C. hiranonis* may both act as markers for leanness in domesticated dogs.

Conclusion

It is believed that these results represent the first species and strain level analysis of microbiome markers of obesity and leanness in domesticated cats and dogs. These findings can greatly inform future studies on how modulation of gut microbiome may help prevent and/or treat obesity in animals.

Example 2

Triplicate bioreactor colon simulators for each of a control (without added mucin), 0.5% added mucin, and 1.0% added mucin were prepared using fecal inoculum of a single healthy adult cat and kept at a constant temperature (39° C.) and anaerobic conditions for the entire duration of the experiment (48 hours). The mucin added was minimally processed porcine gastrointestinal mucin having very low free glycan content (<1%).

Figure 11:
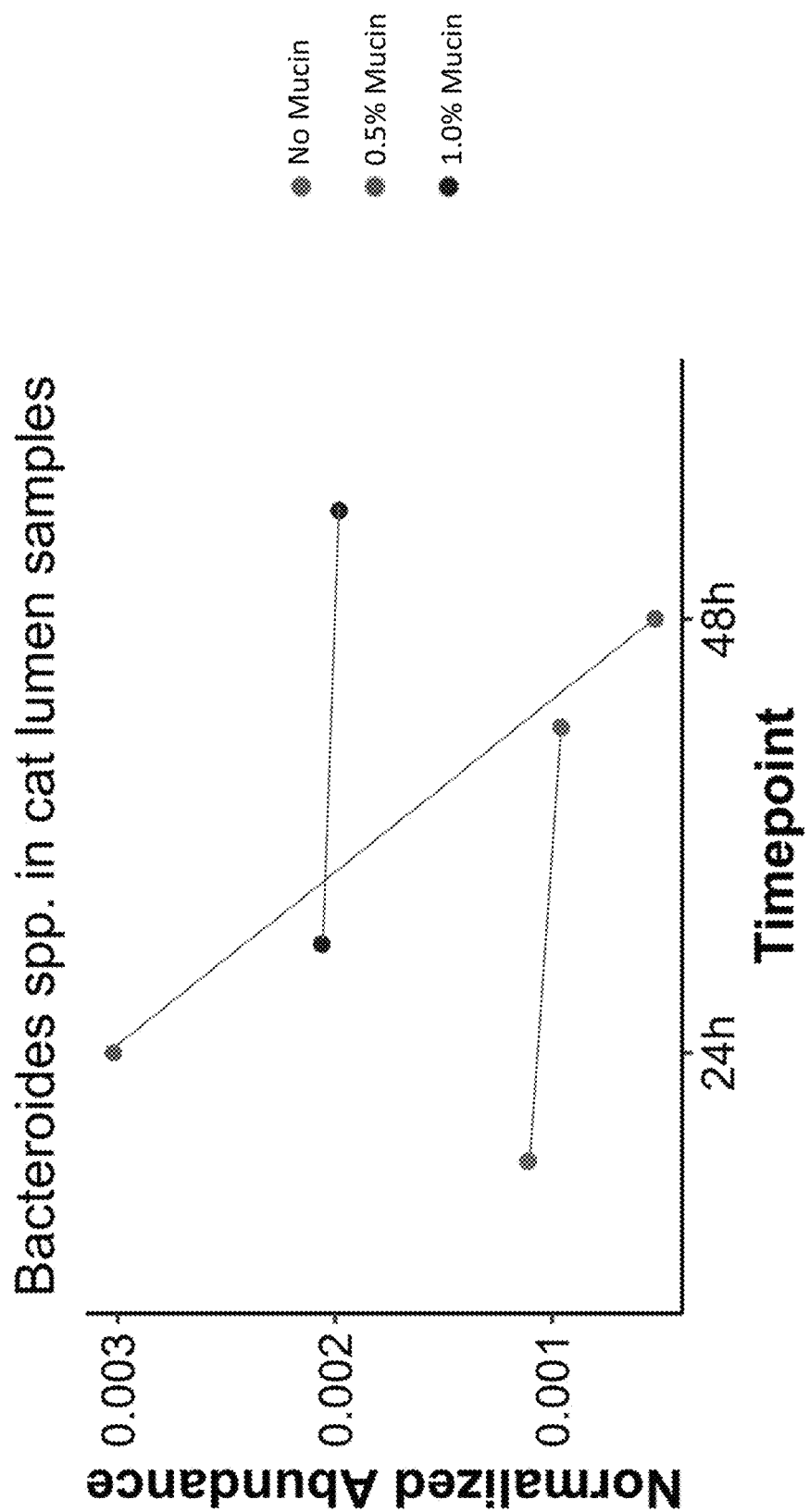
FIG. 11 is a graph showing that the abundance of *Bacteroides* spp. is increased in a colonic simulator bacterial culture inoculated with a cat fecal sample and supplemented with porcine gastrointestinal tract mucins having a less than 1% free glycans (i.e., glycans not part of glycopeptides or glycoproteins).

At 0 hours, 24 hours and 48 hours after addition of the mucin, a sample was taken from each bioreactor, DNA was isolated and the level of *Bacteroides* spp. was measured via sequencing by Bioinnovation Solutions using the PETSEQ workflow for bacterial detection in cats. This consists of molecular assay for library preparation, sequencing, and data analysis and interpretation. As shown in FIG. 11, addition of 1% mucin caused growth of *Bacteroides* spp. An increased level in the feline gut of a *Bacteroides* species is identified in Example 1 as associated with leanness. Thus, the results of FIG. 11 show that the added mucins are a candidate agent for treating, suppressing the likelihood, or preventing obesity in cats.

Those skilled in the art will recognize, or be able to ascertain using no more than routine experimentation, many equivalents to the specific embodiments described herein. The scope of the present invention is not intended to be limited to the Description or the details set forth therein. Articles such as "a", "an" and "the" may mean one or more than one unless indicated to the contrary or otherwise evident from the context. Claims or descriptions that include "or" or "and/or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more element(s), feature(s), or limitation(s) found in any other claim, e.g., any other claim that is dependent on the same base claim. Any one or more claims can be modified to explicitly exclude any one or more embodiment(s), element(s), feature(s), etc. For example, any particular sideroflexin, sideroflexin modulator, cell type, cancer type, etc., can be excluded from any one or more claims.

Where elements are presented as lists, e.g., in Markush group format, each subgroup of the elements is also disclosed, and any element(s) can be removed from the group. For purposes of conciseness only some of these embodiments have been specifically recited herein, but the present disclosure encompasses all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

It should be understood that, unless clearly indicated to the contrary, in any methods claimed herein that include more than one act, the order of the acts of the method is not necessarily limited to the order in which the acts of the method are recited, but the disclosure encompasses embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. It should also be understood that unless otherwise indicated or evident from the context, any product or composition described herein may be considered "isolated". It should also be understood that, where applicable, unless otherwise indicated or evident from the context, any method or step of a method that may be amenable to being performed mentally or as a mental step or using a writing implement such as a pen or pencil, and a surface suitable for writing on, such as paper, may be expressly indicated as being performed at least in part, substantially, or entirely, by a machine, e.g., a computer, device (apparatus), or system, which may, in some embodiments, be specially adapted or designed to be capable of performing such method or step or a portion thereof.

Embodiments or aspects herein may be directed to any agent, composition, article, and/or method described herein. It is contemplated that any one or more embodiments or aspects can be freely combined with any one or more other embodiments or aspects whenever appropriate. For example, any combination of two or more agents, compositions, articles, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

What is claimed is:

1. A method of identifying and treating obesity in a domesticated dog comprising the steps of:
   (a) receiving information as to the expression level of bacterial species *Eubacterium tenue* and *Clostridium hiranonis*-in a biological sample from the domesticated dog relative to a pre-determined threshold expression level of the corresponding bacterial species in a control domesticated dog;
   (b) determining that the domesticated dog is obese if the expression level of the bacterial species measured in step (a) is significantly lower than in the control domesticated dog; and
   (c) treating the domesticated dog determined to be obese in step (b) by administering to the obese dog a therapeutically effective amount of a composition comprising an agent that selectively increases the gut population of one or more bacterial species selected from *Eubacterium tenue* and *Clostridium hiranonis*.

2. The method of claim 1, wherein the biological sample is a fecal sample.

3. The method of claim 1, wherein the agent comprises mucins.

4. The method of claim 1, wherein the agent comprises porcine mucins.

5. The method of claim 4, wherein the porcine mucins are obtained from porcine gastrointestinal tract.

6. The method of claim 5, wherein the agent comprises less than 1% free glycans.

7. The method of claim 1, wherein the agent is one or more bacterial species selected from *Eubacterium tenue* and *Clostridium hiranonis*.

8. A method of treating obesity in a domesticated dog by administering to the dog a therapeutically effective amount of a composition comprising an agent that selectively increases the gut population of both *Eubacterium tenue* and *Clostridium hiranonis*.

9. The method of claim 8, wherein the agent comprises mucins.

10. The method of claim 8, wherein the agent comprises porcine mucins.

11. The method of claim 8, wherein the agent comprises *Eubacterium tenue* and *Clostridium hiranonis*.

12. A method of identifying and treating obesity in a domesticated dog comprising the steps of:
   (a) receiving information as to the expression level of bacterial species *Eubacterium tenue* in a biological sample from the domesticated dog relative to a pre-determined threshold expression level of *Eubacterium tenue* in a control domesticated dog;
   (b) determining that the domesticated dog is obese if the expression level of *Eubacterium tenue* measured in step (a) is significantly lower than in the control domesticated dog; and
   (c) treating the domesticated dog determined to be obese in step (b), by administering to the obese dog a therapeutically effective amount of a composition comprising an agent that selectively increases the gut population of *Eubacterium tenue*.

13. The method of claim 12, wherein the biological sample is a fecal sample.

14. The method of claim 12, wherein the agent comprises mucins.

15. The method of claim 12, wherein the agent comprises porcine mucins.

16. The method of claim 15, wherein the porcine mucins are obtained from porcine gastrointestinal tract.

17. The method of claim 16, wherein the agent comprises less than 1% free glycans.

18. The method of claim 12, wherein the agent comprises *Eubacterium tenue*.

* * * * *